US008216610B2

(12) United States Patent
Roberts et al.

(10) Patent No.: US 8,216,610 B2
(45) Date of Patent: Jul. 10, 2012

(54) ORAL PARACETAMOL FORMULATIONS

(75) Inventors: Michael Stephen Roberts, West Lake (AU); Ruoying Jiang, Sherwood (AU); Keivan Bezanehtak, Rosebery (AU); Greg Andrew Davey, Sinnamon Park (AU); George Alexander Davidson, Larnook (AU); Geraldine Ann Elliott, Mount Ommaney (AU); Stephen Douglas Chandler, Mayfield (AU); Mantu Sarkar, Fairfield (AU)

(73) Assignee: Imaginot Pty Ltd., Queensland (AU)

( * ) Notice: Subject to any disclaimer, the term of this patent is extended or adjusted under 35 U.S.C. 154(b) by 0 days.

(21) Appl. No.: 11/604,972

(22) Filed: Nov. 27, 2006

(65) Prior Publication Data
US 2007/0141144 A1    Jun. 21, 2007

Related U.S. Application Data

(63) Continuation-in-part of application No. 11/138,262, filed on May 27, 2005, now abandoned.

(60) Provisional application No. 60/575,477, filed on May 28, 2004.

(51) Int. Cl.
*A61K 31/167* (2006.01)
*A61K 31/12* (2006.01)
*A01N 35/00* (2006.01)

(52) U.S. Cl. .......... 424/489; 514/675; 514/676; 424/464

(58) Field of Classification Search ............... 514/183
See application file for complete search history.

(56) References Cited

U.S. PATENT DOCUMENTS

| | | | |
|---|---|---|---|
| 3,390,049 | A | 6/1968 | Rednick |
| 3,851,032 | A * | 11/1974 | Andrews et al. ............ 424/78.24 |
| 4,309,408 | A | 1/1982 | Pathak et al. |
| 4,687,662 | A | 8/1987 | Schobel |
| 4,704,269 | A | 11/1987 | Korab |
| 4,704,405 | A | 11/1987 | O'Neill et al. |
| 4,824,664 | A | 4/1989 | Tarral et al. |
| 4,834,966 | A | 5/1989 | Gazzaniga et al. |
| 4,942,039 | A | 7/1990 | Duvall et al. |
| 5,019,399 | A | 5/1991 | Appelgren et al. |
| 5,064,656 | A | 11/1991 | Gergely et al. |
| 5,075,291 | A | 12/1991 | DuRoss |
| 5,102,665 | A | 4/1992 | Schaeffer |
| 5,118,528 | A | 6/1992 | Fessi et al. |
| 5,145,684 | A | 9/1992 | Liversidge et al. |
| 5,158,779 | A | 10/1992 | Gergely et al. |
| 5,178,878 | A | 1/1993 | Wehling et al. |
| 5,225,197 | A | 7/1993 | Bolt et al. |
| 5,260,304 | A | 11/1993 | Gergely et al. |
| 5,262,171 | A | 11/1993 | Login et al. |
| 5,273,759 | A | 12/1993 | Simmons |
| 5,312,626 | A | 5/1994 | Gergely et al. |
| 5,348,475 | A | 9/1994 | Waknine et al. |
| 5,348,745 | A | 9/1994 | Daher |
| 5,419,898 | A | 5/1995 | Ikejiri et al. |
| 5,424,075 | A | 6/1995 | Daher et al. |
| 5,425,950 | A | 6/1995 | Dandiket et al. |
| 5,527,540 | A | 6/1996 | Gergely et al. |
| 5,587,179 | A | 12/1996 | Gergely et al. |
| 5,593,693 | A | 1/1997 | Gergely et al. |
| 5,639,475 | A | 6/1997 | Bettman et al. |
| 5,670,170 | A | 9/1997 | Grimmett et al. |
| 5,709,886 | A | 1/1998 | Bettman et al. |
| 5,733,578 | A | 3/1998 | Hunter et al. |
| 5,750,145 | A | 5/1998 | Patell |
| 5,759,575 | A | 6/1998 | Gergely et al. |
| 5,762,951 | A | 6/1998 | Maasz et al. |
| 5,792,473 | A | 8/1998 | Gergely et al. |
| 5,807,577 | A | 9/1998 | Ouali |
| 5,807,578 | A | 9/1998 | Acosta-Cuello et al. |
| 5,814,337 | A | 9/1998 | Meerfield et al. |
| 5,840,737 | A | 11/1998 | Phillips |
| 5,854,226 | A | 12/1998 | Penkler et al. |
| 5,858,410 | A | 1/1999 | Muller et al. |
| 5,863,559 | A | 1/1999 | Phillips et al. |
| 5,869,095 | A | 2/1999 | Gergely et al. |
| 5,914,129 | A | 6/1999 | Mauskop |
| 5,922,355 | A | 7/1999 | Parikh et al. |
| 5,962,022 | A | 10/1999 | Bolt et al. |
| 6,020,001 | A | 2/2000 | Phillips et al. |
| 6,051,254 | A | 4/2000 | Merrifield et al. |
| 6,077,536 | A | 6/2000 | Merrifield et al. |
| 6,149,938 | A | 11/2000 | Bonadeo |

(Continued)

FOREIGN PATENT DOCUMENTS

CA    2326809    8/2001

(Continued)

OTHER PUBLICATIONS

Ivanov et al., Direct cytotoxicity of non-steroidal anti-inflammatory drugs in acidic media: model study on human erythrocytes with DIDS-inhibited anion exchanger, 2002, Pharmazie, vol. 57 (12), p. 848, abstract only.*
Particle characterization in Excipients, drug products, and drug substances, accessed Oct. 7, 2009. http://www.geochem.sgs.com/Isnewsqc/Isnewsqc_july_issue/particle_characterisation_in_excipients_drug_products_and_drug_substances_Iss_newsletter.htm.*
US Pharmacopeia, Particle Size Distribution Estimation by Analytical Sieving, accessed Oct. 7, 2009. http://www.pharmacopeia.cn/v29240/usp29nf24s0_c786.html.*
Moolenaar et al., Biopharmaceutics of rectal adminstration of drugs in man, 1979, Pharmaceutish Weekblad Scientific Edition, vol. 1, pp. 689-694.*

(Continued)

*Primary Examiner* — Jeffrey S. Lundgren
*Assistant Examiner* — Meghan Finn
(74) *Attorney, Agent, or Firm* — Kenyon & Kenyon LLP

(57) ABSTRACT

The present invention relates generally to formulations comprising paracetamol. More particularly, the present invention provides a swallow formulation comprising paracetamol which facilitates the rapid delivery of paracetamol into the circulatory system following oral administration. The present invention further relates to methods for inducing efficient pain relief including an analgesic effect by the administration of the paracetamol formulation.

40 Claims, 3 Drawing Sheets

U.S. PATENT DOCUMENTS

| | | | |
|---|---|---|---|
| 6,156,506 | A | 12/2000 | Yamamoto et al. |
| 6,160,020 | A | 12/2000 | Ohannesian et al. |
| 6,165,506 | A | 12/2000 | Jain et al. |
| 6,171,617 | B1 | 1/2001 | Gruber |
| 6,197,336 | B1 | 3/2001 | Grassano et al. |
| 6,210,711 | B1 | 4/2001 | Aiache et al. |
| 6,214,386 | B1 | 4/2001 | Santus et al. |
| 6,217,907 | B1 | 4/2001 | Hunter et al. |
| 6,242,002 | B1 | 6/2001 | Tritthart et al. |
| 6,245,353 | B1 | 6/2001 | Tritthart et al. |
| 6,258,814 | B1 | 7/2001 | Martin |
| 6,274,172 | B1 | 8/2001 | Mention |
| 6,277,409 | B1 | 8/2001 | Luber |
| 6,284,272 | B1 | 9/2001 | Chiesi et al. |
| 6,309,668 | B1 | 10/2001 | Bastin et al. |
| 6,316,025 | B1 | 11/2001 | Grattan |
| 6,348,485 | B1 | 2/2002 | Ohkawa et al. |
| 6,350,470 | B1 | 2/2002 | Pather et al. |
| 6,368,627 | B1 | 4/2002 | Phillips et al. |
| 6,383,471 | B1 | 5/2002 | Chen et al. |
| 6,391,337 | B2 | 5/2002 | Hunter et al. |
| 6,432,450 | B1 | 8/2002 | Gergely et al. |
| 6,479,551 | B1 | 11/2002 | Plachetka et al. |
| 6,488,961 | B1 | 12/2002 | Robinson et al. |
| 6,489,346 | B1 | 12/2002 | Phillips |
| 6,509,036 | B2 | 1/2003 | Pather et al. |
| 6,514,531 | B1 | 2/2003 | Alaux et al. |
| 6,589,556 | B2 | 7/2003 | Cherukuri |
| 6,620,433 | B2 | 9/2003 | Martin et al. |
| 6,638,535 | B2 | 10/2003 | Lemmens et al. |
| 6,641,838 | B2 | 11/2003 | Pather et al. |
| 6,645,988 | B2 | 11/2003 | Phillips |
| 6,649,186 | B1 | 11/2003 | Robinson et al. |
| 6,667,056 | B2 | 12/2003 | Chiesi et al. |
| 6,699,885 | B2 | 3/2004 | Phillips |
| 6,750,237 | B1 | 6/2004 | Dearn et al. |
| 6,780,882 | B2 | 8/2004 | Phillips |
| 2001/0014340 | A1 | 8/2001 | Ohta et al. |
| 2002/0031547 | A1 | 3/2002 | Takagi et al. |
| 2002/0034540 | A1 | 3/2002 | Price |
| 2002/0071864 | A1 | 6/2002 | Kim et al. |
| 2002/0076439 | A1 | 6/2002 | Pather et al. |
| 2002/0110578 | A1 | 8/2002 | Pather et al. |
| 2003/0003146 | A1 | 1/2003 | Takagi et al. |
| 2003/0035833 | A1 | 2/2003 | He |
| 2003/0069213 | A1 | 4/2003 | H et al. |
| 2003/0091626 | A1 | 5/2003 | Katsuta |
| 2003/0096013 | A1 | 5/2003 | Werling et al. |
| 2003/0133976 | A1 | 7/2003 | Pather et al. |
| 2003/0170301 | A1 | 9/2003 | Wehling |
| 2003/0175355 | A1 | 9/2003 | Tobyn et al. |
| 2003/0185886 | A1 | 10/2003 | Lee et al. |
| 2003/0203007 | A1 | 10/2003 | Ukai et al. |
| 2003/0215500 | A1 | 11/2003 | Ohta et al. |
| 2003/0236183 | A1 | 12/2003 | De Bruijn et al. |
| 2004/0014680 | A1 | 1/2004 | Nakagami et al. |
| 2004/0071772 | A1 | 4/2004 | Narita et al. |
| 2004/0170681 | A1 * | 9/2004 | Grattan ............ 424/465 |
| 2004/0204475 | A1 | 10/2004 | Humphrey |
| 2004/0247677 | A1 * | 12/2004 | Oury et al. ........ 424/472 |
| 2005/0032867 | A1 | 2/2005 | Baker et al. |
| 2005/0042281 | A1 | 2/2005 | Singh et al. |
| 2005/0136120 | A1 * | 6/2005 | Kugelmann et al. ...... 424/489 |
| 2005/0147671 | A1 | 7/2005 | Reiner et al. |
| 2005/0276847 | A1 | 12/2005 | Roberts et al. |

FOREIGN PATENT DOCUMENTS

| | | |
|---|---|---|
| GB | 1 410 909 | 10/1975 |
| GB | 2 103 087 | 2/1983 |
| WO | 9744023 | 11/1997 |
| WO | 98/38983 | 9/1998 |
| WO | 02/100391 | 12/2002 |
| WO | 03/047552 | 12/2002 |
| WO | 2002/100319 | 12/2002 |
| WO | WO 03/026610 | 4/2003 |
| WO | 2003/047552 | 6/2003 |
| WO | 03/074029 | 9/2003 |
| WO | WO 03/082247 A2 * | 10/2003 |
| WO | 2004/004705 | 1/2004 |
| WO | WO 2004/012708 A1 * | 2/2004 |
| WO | 2004/017976 | 3/2004 |
| WO | WO 2005/041938 | 5/2005 |
| WO | WO 2005/115344 | 12/2005 |

OTHER PUBLICATIONS

Kolloffel et al., Rectal administration of paracetamol a comparison of a solution and suppositories in adult volunteers, 1996, Pharmacy World and Science, vol. 18, No. 1, pp. 26-29.*

Rubinstein et al., The effect of Excipient Solubility on the in-vitro and in-vivo properties of bendrofluazide tablets 5mg, 1977, vol. 3, No. 5, pp. 439-450, Abstract Only.*

Barbara Ameer et al., *Absolute and Relative Bioavailability of Oral Acetaminophen Preparations*, 72(8) J. Pharm. Sci., 955-958 (1983).

Tim Grattan et al., *A Five Way Crossover Human Volunteer Study to Compare the Pharmacokinetics of Paracetamol Following Oral Administration of Two Commercially Available Paracetamol Tablets and Three Development Tablets Containing Paracetamol in Combination With Sodium Bicarbonate or Calcium Carbonate*, European J. Pharmacetics and Biopharmaceutics, 225-299 (2000).

J.C. Nielsen et al. *Analgesic Efficacy of Immediate and Sustained Release Paracetamol and Plasma Concentration of Paracetamol. Double Blind, Placebo-Controlled Evaluation Using Painful Laser Stimulation*, 42 European Journal of Clinical Pharmacology, 261-264 (1992).

L.F. Prescott et al. *Gastrointestinal Absorption of Drugs*, 58(5) The Medical Clinics of North America, 907-916 (1974).

Laurie F. Prescott, *Paracetamol: Past, Present, and Future*, 7 American Journal of Therapeutics, 143-147 (2000).

Barry H. Rumack, et al., *Acetaminophen Overdose: Incidence, Diagnosis, and Management in 416 Patents*, 62 (Suppl) Pediatrics, 898-903 (1978).

Roger H. Rumble et al., *Effect of Posture and Sleep on Pharmacokinetics of Paracetamol (Acetaminophen) and Its Metabolites*, 20(1) Clinical Pharmacokinetics, 167-173 (1991).

Babalola et al., "Correlation between in vitro and in vivo parameters of commercial paracetamol tablets," (2001), Afr. J. Med Sci, 30, pp. 275-280.

Borin et al., "Single dose bioavailability of acetaminophen following oral administration," (1989), International Journal of Pharmaceutics, 54, pp. 199-209.

Dominguez et al., "Bioequivalence study of paracetamol tablets: In vitro-in vivo correlation," (2000), Drug Development and Industrial Pharmacy, 26(8), pp. 821-828.

Hedges et al., "A comparison of the absorption of effervescent preparations of paracetamol and penicillin V (Phenoxymethylpenicillin) with solid dose forms of these drugs," (1974), J. Clin. Pharmacol., 14, pp. 363-368.

Hekimoglu et al., "Comparative bioavailability of three commercial acetaminophen tablets," (1987), International J. Clin. Pharmacol., 25(2), pp. 93-96.

Hekimoglu et al., "Comparative bioavailability of three batches of four commercial acetaminophen tablets," (1991), European Journal of Drug Metabolism and Pharmacokinetics, pp. 228-232.

Ishikawa et al., "Pharmacokinetics of acetaminophen from rapidly disintegrating compressed tablet prepared using microcrystalline cellulose (PH-M-06) and spherical sugar granules," Chem. Pharm. Bull. (2001), 49(2), pp. 230-232.

Retaco et al., "Bioavailibility study of paracetamol tablets in saliva and urine," (1996), European Journal of Drug Metabolism and Pharmacokinetics, 4, pp. 295-300.

Rygnestad et al., "Absorption of effervescent paracetamol tablets relative to ordinary paracetamol tablets in healthy volunteers," (2000), Eur J. Clin Pharmacol, 56, pp. 141-143.

Sevilla-Tirado et al., "Bioavailability of two new formulations of paracetamol compared with three marketed formulations, in healthy volunteers," (2003), Methods Find Exp Clin Pharmacol, 25(7), pp. 531-535.

Soininen et al., "Dissolution rate of different kinds of granulated micronized paracetamol with adjuvant incorporated either inter-or intragramularly," (1981), Acta Pharm. Fenn, 90, pp. 153-162.

Sotiropoulus et al., "Comparative bioavailability of three commercial acetaminophen tablets," (1981), Journal of Pharmaceutical Sciences, 70(4), pp. 422-425.

Office Action from related U.S. Appl. No. 11/597,341, mailed May 12, 2010.

Garekani et al. Drug Dev. Ind. Pharm. 2a(2): 173-179 (2003).

Goldberg et al, J.Pharm.Biophrm 49(3):225-229 (2000).

M. Iwuagwu, A. Onyekwell, Tropical J. Pharm Res. 1(1):29-37 (2002).

Walters, J. Pharm. Pharmacol. 20:228s-231s (1968).

Amendment dated Aug. 12, 2010 in U.S. Appl. No. 11/597,341.

Non-Final Office Action dated May 12, 2010 issued in U.S. Appl. No. 11/597,341.

Final Office Action dated Oct. 25, 2010 issued in U.S. Appl. No. 11/597,341.

L. Kalantzi, et al. *"Biowaiver monographs for immediate release solid oral dosage forms: Acetaminophen (paracetamol)"* Journal of Pharmaceutical Sciences vol. 95, Issue 1, pp. 4-14, 2006.

Office Action dated Mar. 15, 2012 issued in U.S. Appl. No. 12/085,645.

Office Action dated Mar. 21, 2012 issued in U.S. Appl. No. 11/597,341.

http://www.ncbi.nlm.nih.gov/pubmedhealth/PMH0000003/ viewed on Mar. 7, 2012, 2009.

* cited by examiner

Fig 1  Paracetamol Dissolution Profiles in 900 mL 0.05 N hydrochloric acid at 30 rpm
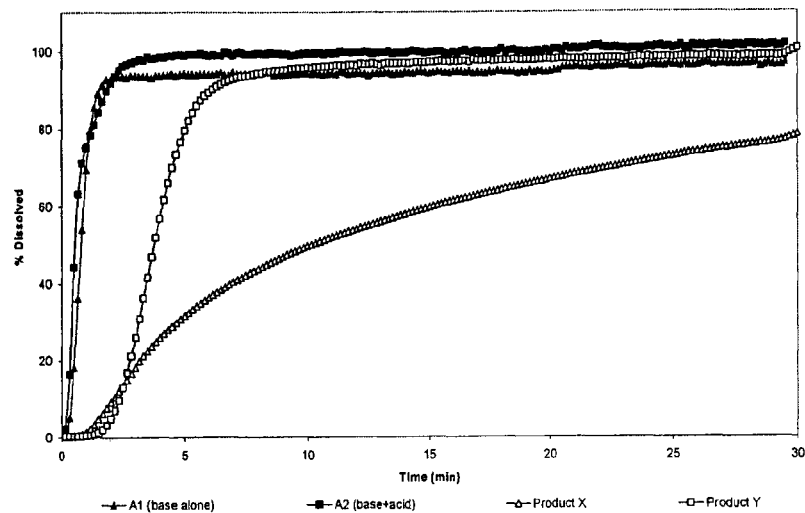
Fig 2  Paracetamol Dissolution Profiles in 900 mL 0.0033 N hydrochloric acid at 30 rpm.
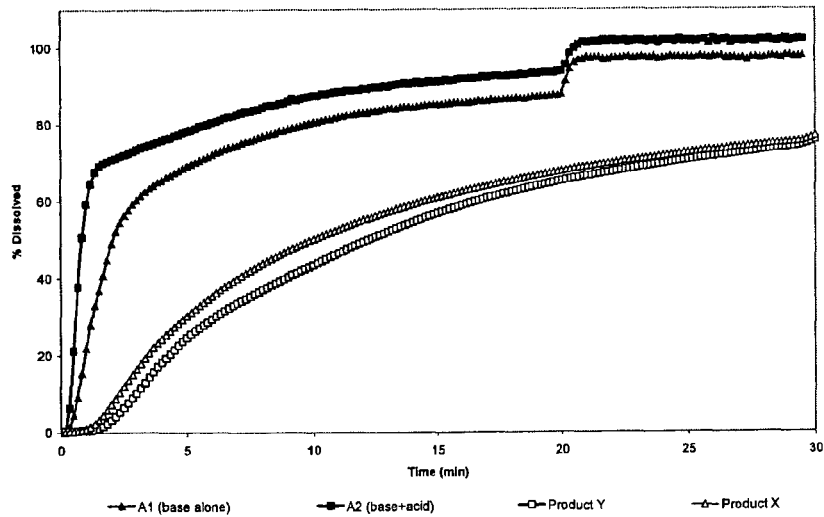

Fig 3    Paracetamol Dissolution Profiles in 900 mL 0.0033 N hydrochloric acid at 0 rpm
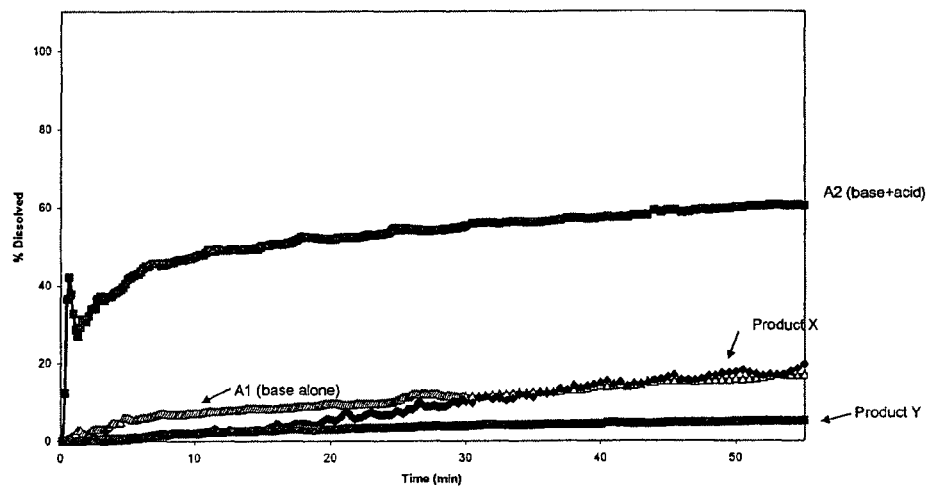
Fig 4    Paracetamol and Tramadol Hydrochloride Dissolution Profiles in 900 mL 0.05 N hydrochloric acid at 30 rpm
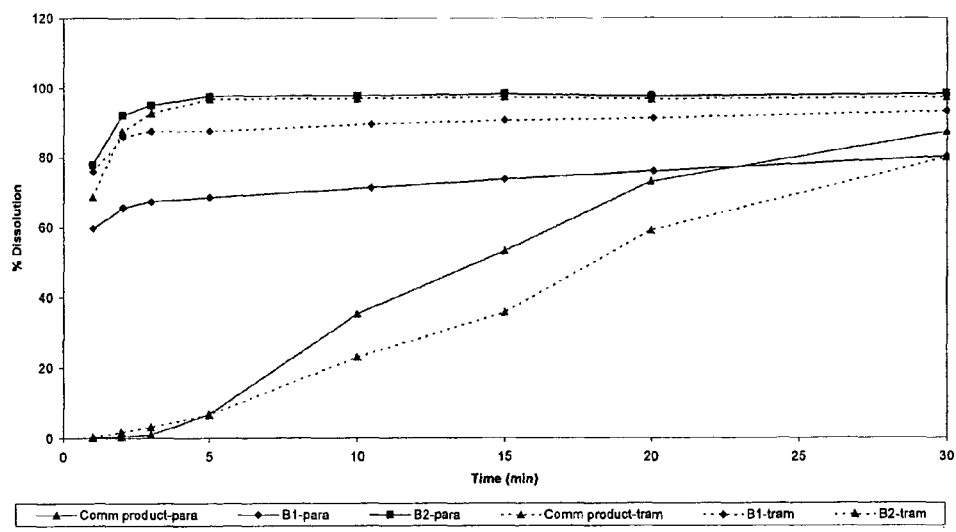

Fig 5  Paracetamol and Tramadol Hydrochloride Dissolution Profiles in 900 mL 0.0033 N hydrochloric acid at 30 rpm
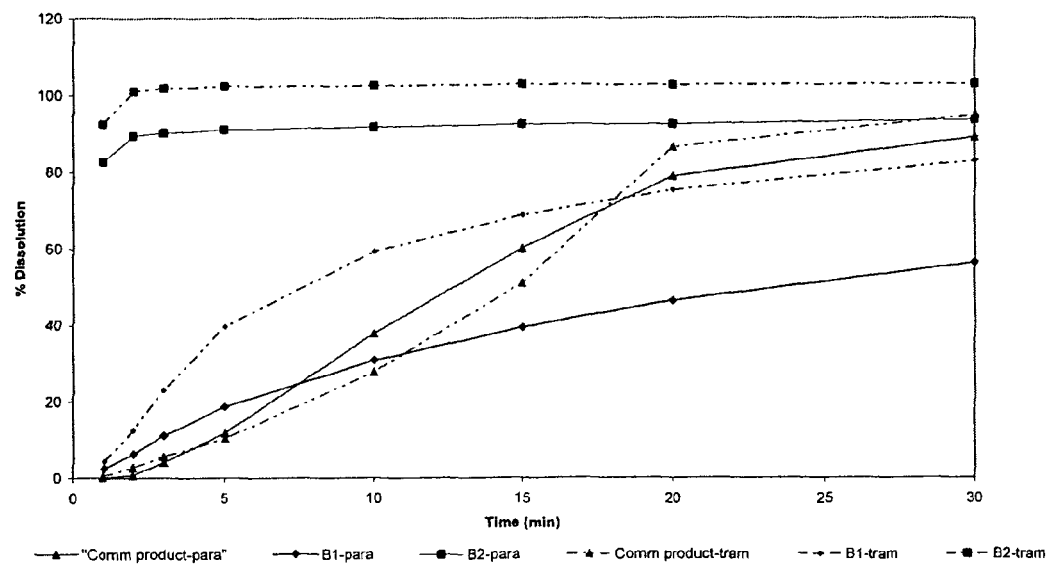
Fig 6  Paracetamol and Tramadol Hydrochloride Dissolution Profiles in 900 mL 0.0033 N hydrochloric acid at 0 rpm
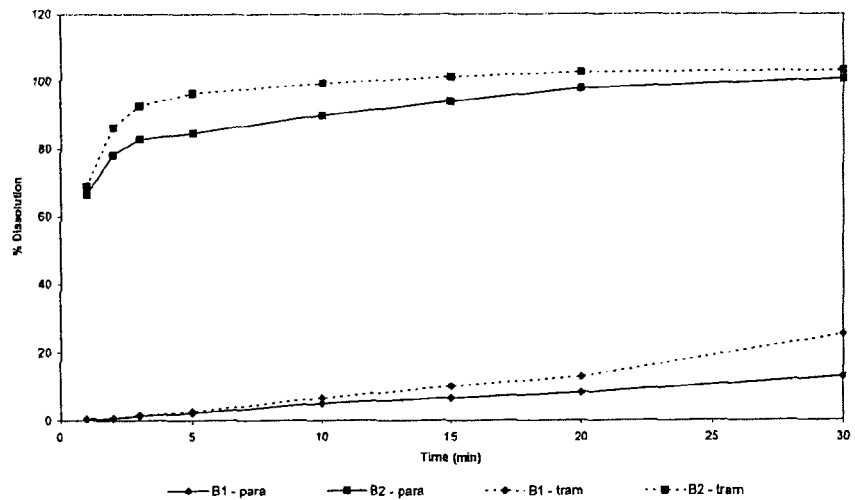

ORAL PARACETAMOL FORMULATIONS

RELATED APPLICATIONS

This application is a continuation-in-part of U.S. patent application Ser. No. 11/138,262, filed May 27, 2005, now abandoned, which claims priority of U.S. Provisional Patent Application No. 60/575,477, filed May 28, 2004.

BACKGROUND OF THE INVENTION

1. Field of the Invention

The present invention relates generally to formulations comprising paracetamol. More particularly, the present invention provides a swallow formulation comprising paracetamol which facilitates the rapid delivery of paracetamol into the circulatory system following oral administration. The present invention further relates to methods for inducing efficient pain relief including an analgesic effect by the administration of the paracetamol formulation.

2. Description of the Prior Art

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

Paracetamol, also known as N-acetyl-p-aminophenol, acetaminophen and APAP, is an analgesic and antipyretic agent and is widely used in prescription and non-prescription medicines. Paracetamol was first marketed in the 1950's and is now a commonly used agent (Prescott *Am. J. Ther.* 7(2): 143-147 2000). The precise mechanism of paracetamol's analgesic and antipyretic effect remains unclear. However, some studies have suggested that the rate of administration is a factor (Nielsen et al. *Eur. J. Clin. Pharmacol.* 42(3): 261-264, 1992, Luthy, et al. *Schweiz Med. Wochenschr* 123 (*Suppl* 50)/II:406, 1993). Accordingly, increasing the rate of absorption of paracetamol should enable a greater and more rapid analgesic effect after oral dosing. In this regard, oral delivery is the most convenient and acceptable route of drug administration to end users, especially for a drug administered at high doses and frequency, such as paracetamol.

Improving the rate and extent of absorption of oral formulations of compounds has been the subject of substantial research. In general, once a solid swallow composition reaches the stomach, it undergoes disintegration and/or dissolution and passes into the small intestine where the active ingredient is absorbed across intestinal walls into the circulatory system via the portal vein and liver before reaching the site of action.

Rates of absorption are often assessed by comparing standard pharmacokinetic parameters such as the time to peak plasma concentration ($T_{max}$) and the peak plasma concentration ($C_{max}$). The extent of absorption is assessed by the area under the plasma concentration-time curve (AUC). A short $T_{max}$ has been used to indicate rapid absorption. The FDA Guidance for Industry on Bioavailability and Bioequivalence Studies for Orally Administered Products (2003) and related publications (Chen et al, *Clin. Pharmacokinet.* 40(8):565-72, 2001) recommend the use of partial AUC as an early exposure measure, such that a high partial AUC will be an indicator of rapid absorption. The parameters for known formulations vary greatly between subjects. The parameters also vary depending on aspects of the study protocol such as the sampling scheduling, subject posture and general subject health.

Values quoted in this specification are given as mean±standard deviation unless otherwise noted.

For paracetamol tablets supplied by McNeil, a $T_{max}$ value has been quoted as 45.6 minutes with a standard error of 7.2 minutes with a corresponding $C_{max}$ value of 11.99 mg·L$^{-1}$ with a standard error of 1.02 (Ameer et al., *J. Pharm. Sci,* 72:955-958, 1983)). Other values quoted include a $T_{max}$ of 35.6±27.7 minutes and $C_{max}$ of 9.47±4.18 mg·L$^{-1}$ (Rumble et al., *Clin. Pharmacokinet.* 20 (2): 167-173, 1991), a $T_{max}$ of 1.82 hours with a standard error of 0.46 hours and a $C_{max}$ of 20.4±3.2 mg·L$^{-1}$ for Paralen tablets and for Panadol tablets, a $T_{max}$ of 35 minutes and as high as 77 minutes and a $C_{max}$ value of 17.02±6.04 mg·L$^{-1}$ (Grattan et al., *Eur. J Pharm. Biopharm.* 49(3):225-229, 2000).

The range of paracetamol plasma concentrations for e effective analgesia in humans is quoted to be about 5-20 µg·mL$^{-1}$. (Prescott, *Medical Clinics of North America,* 58:907-916, 1974). For antipyresis a paracetamol concentration of 10-20 µg·mL$^{-1}$ has been shown to be effective (Rumack et al, *Pediatrics* 62(*Suppl*):898-903, 1978).

In a submission compiled by McNeil in 2002 in relation to Tylenol to demonstrate safety and efficacy of paracetamol to the United States Food and Drug Administration (USFDA), the effective concentration which elicits 50% of the maximum drug response ($EC_{50}$) was estimated to be between 15.2 µg·mL$^{-1}$ and 16.55 µg·mL$^{-1}$ (McNeil submission to FDA, 2002)

Prescott (1974, supra) reported there may be as much as an 80-fold range in concentrations 1 hour after therapeutic doses of paracetamol were administered in 43 patients. He concluded that pharmacokinetic variability impacts on response rates for analgesics. In fact, many patients may never achieve a therapeutic effect.

In U.S. Pat. No. 6,316,025, Grattan describes a swallow tablet of paracetamol containing 300 mg to 1000 mg of sodium bicarbonate per tablet and a paracetamol to sodium bicarbonate ratio of between 0.74 and 1. Grattan et al. (2000 supra) subsequently reported that a formulation with 630 mg sodium bicarbonate gave a $T_{max}$ of 17.5±4.95 minutes and a $C_{max}$ of 29.79±9.06 mg·L$^{-1}$. It was suggested that this was due to an osmotic effect of sodium bicarbonate, which would be isotonic when ingested with 100 mL of water.

US Patent Application No. 20040204475 describes a formulation containing sodium bicarbonate and eletriptan. The sodium bicarbonate is administered in an amount to obtain a duodenal concentration approximately isotonic with serum (150 mmol). The formulations exemplified all contained 630 mg sodium bicarbonate.

US Patent Application No. 20040170681 describes a paracetamol formulation containing less than 100 mg sodium bicarbonate per tablet. About 90% of the paracetamol is described as being released from this formulation in 15 minutes using United States Pharmacopoeia (USP) dissolution apparatus 2 with 900 mL 0.05 N hydrochloric acid at 30 rpm and 37° C. A formulation was exemplified which resulted in an area under the plasma concentration-time curve at 20 minutes after administration (AUC20) of 17 µg·min·mL$^{-1}$ in fed subjects when given as a 1000 mg paracetamol dose.

United Kingdom Patent No. 2103087 describes the use of antacids in paracetamol tablets. Antacids including calcium carbonate and sodium bicarbonate were used in the range of 60-1200 mg. The greatest increase was noted with 225 mg of sodium bicarbonate which showed an increase in the rate of absorption of paracetamol of between 7% and 31% compared with conventional paracetamol tablets. The shortest $T_{max}$ reported was 29 minutes.

In accordance with the present invention, paracetamol formulations and in particular swallow formulations are defined in which the parameters for drug dissolution and absorption have been significantly improved.

SUMMARY OF THE INVENTION

The present invention relates generally to paracetamol formulations in the form of fast absorbing oral delivery systems. In particular, the present invention provides a swallow formulation comprising paracetamol, one or more pH modulating agents, and one or more agents which facilitate water uptake. The paracetamol is incorporated as a rapidly dissolving form of paracetamol.

The present invention provides, therefore, a swallow formulation comprising a rapidly dissolving form of paracetamol, a pH modulating agent and an agent which facilitates water uptake, wherein the pH modulating agent is in an amount sufficient to neutralize from about 0.6 mL to about 110 mL 0.1 N hydrochloric acid and/or to neutralize from about 0.06 mmol to about 11 mmol acid and wherein at least about 70% of the paracetamol in the swallow formulation is dissolved from the swallow formulation within 180 seconds in USP dissolution apparatus 2 with 900 mL 0.05 N hydrochloric acid at 30 rpm and 37° C.

The present invention further provides, a swallow formulation comprising a rapidly dissolving form of paracetamol, a pH modulating agent and an agent which facilitates water uptake, wherein the pH modulating agent is in an amount sufficient to neutralize from about 0.6 mL to about 110 mL 0.1 N hydrochloric acid and/or to neutralize from about 0.06 mmol to about 11 mmol acid and wherein at least about 5% of the paracetamol in the swallow formulation is dissolved from the swallow formulation within 300 seconds in USP dissolution apparatus 2 with 900 mL 0.05 N hydrochloric acid at 0 rpm and 37° C.

The present invention also provides a swallow formulation comprising paracetamol having a volume median diameter ($D_{50}$) of less than 350 μm and a surface area of greater than 0.07 $m^2 \cdot g^{-1}$, a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake into the formulation;
wherein
  (a) at least about 5% of the paracetamol is dissolved from the swallow formulation within 300 seconds at 0 rpm, and
  (b) at least about 70% of the paracetamol is dissolved from the swallow formulation within 180 seconds at 30 rpm, when the dissolution is measured in United States Pharmacopoeia (USP) dissolution apparatus 2 with 900 mL 0.0033 N hydrochloric acid at 37° C.

Preferably at least about 20% or more preferably at least about 40% of the paracetamol is dissolved form the swallow formulation within 300 seconds.

A rapidly dissolving form of paracetamol includes paracetamol having a volume median diameter ($D_{50}$) of less than 350 μm and a surface area of greater than 0.07 $m^2 \cdot g^{-1}$. It also includes any paracetamol preparation which exhibits a dissolution rate in USP dissolution apparatus 2 using 900 mL of 0.05 N hydrochloric acid at 30 rpm and 37° C. of at least 30% in 180 seconds.

Accordingly, another aspect of the present invention is directed to a swallow formulation comprising a form of paracetamol having a volume median diameter ($D_{50}$) of less than 350 μm and a surface area of greater than 0.07 $m^2 \cdot g^{-1}$; a pH modulating agent in an amount sufficient to neutralize from about 0.6 mL to about 110 mL 0.1 N hydrochloric acid and/or to neutralize from about 0.06 mmol to about 11 mmol acid; and an agent which facilitates water uptake; wherein at least 70% of the paracetamol is dissolved from the swallow formulation within 180 seconds in USP dissolution apparatus 2 with 900 mL 0.05 N hydrochloric acid at 30 rpm and 37° C.

In another embodiment, the present invention contemplates a swallow formulation comprising a form of paracetamol which exhibits a dissolution rate in USP dissolution apparatus 2 using 900 mL of 0.05 N hydrochloric acid at 30 rpm and 37° C. of at least 30% in 180 seconds; a pH modulating agent in an amount sufficient to neutralize from about 0.6 mL to about 110 mL 0.1 N hydrochloric acid and/or to neutralize from about 0.06 mmol to about 11 mmol of 0.1 N hydrochloric acid; and an agent which facilitates water uptake; wherein at least 70% of the paracetamol is dissolved from the swallow formulation within 180 seconds in USP dissolution apparatus 2 with 900 mL 0.05 N hydrochloric acid at 30 rpm and 37° C.

The swallow formulation of the present invention achieves on administration of 1000 mg paracetamol, a mean AUC20 (i.e. area under the plasma concentration-time curve at 20 minutes after administration) of more than 150 $min \cdot mg \cdot L^{-1}$ in fasted healthy human subjects.

Accordingly, another aspect of the present invention provides a swallow formulation comprising a form of paracetamol having a volume median diameter ($D_{50}$) of less than 350 μm and a surface area of greater than 0.07 $m^2 \cdot g^{-1}$; a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake; wherein an administration of 1000 mg paracetamol achieves a mean AUC20 of more than 150 $min \cdot mg \cdot L^{-1}$ in fasted healthy human subjects.

In a related aspect, the present invention provides a swallow formulation comprising a form of paracetamol which exhibits a dissolution rate in USP dissolution apparatus 2 using 900 mL of 0.05 N hydrochloric acid at 30 rpm and 37° C. of at least 30% in 180 seconds; a pH modulating agent in an amount sufficient to neutralize from about 0.6 mL to about 110 mL 0.1 N hydrochloric acid and/or to neutralize from about 0.06 mmol to about 11 mmol acid; and an agent which facilitates water uptake; wherein an administration of 1000 mg paracetamol achieves a mean AUC20 of more than 150 $min \cdot mg \cdot L^{-1}$ in fasted healthy human subjects.

Another aspect of the invention provides a dosage form such as a coated tablet, uncoated tablet, capsule, powder, paste, cachet, colloid, gel or melt.

The present invention further contemplates a method for treating therapeutic indications including an analgesic or antipyretic effect in a human subject said method comprising administering to said subject a pain relieving effective amount of a swallow formulation comprising a rapidly dissolving form of paracetamol having a volume median diameter ($D_{50}$) of less than 350 μm and a surface area of greater than 0.07 $m^2 \cdot g^{-1}$ with a pH modulating agent and an agent which facilitates water uptake into to the swallow formulation, wherein the pH modulating agent is in an amount sufficient to neutralize from about 0.6 mL to about 110 mL 0.1 N hydrochloric acid and/or to neutralize from about 0.06 mmol to about 11 mmol of acid and wherein at least about 70% of the paracetamol in the swallow formulation is dissolved from the swallow formulation within 180 seconds in USP dissolution apparatus 2 with 900 mL 0.05 N hydrochloric acid at 30 rpm and 37° C.

The present invention is further directed to the use of a form of paracetamol which achieves on administration of 1000 mg paracetamol, a mean AUC20 of more than 150 min·mg·L$^{-1}$ in fasted healthy human subjects in the manufacture of a medicament for the inducement of pain relief in a human subject.

In another embodiment, the present invention contemplates a method for treating pain or fever in a human subject said method comprising administering to said subject a pain relieving or fever reducing effective amount of a swallow formulation comprising a rapidly dissolving form of paracetamol having a volume median diameter ($D_{50}$) of less than 350 μm and a surface area of greater than 0.07 m$^2$·g$^{-1}$ with a pH modulating agent and an agent which facilitates water uptake into to the swallow formulation, wherein the pH modulating agent is in an amount sufficient to neutralize from about 0.6 mL to about 110 mL 0.1 N hydrochloric acid and/or to neutralize from about 0.06 mmol to about 11 mmol of acid and wherein an administration of 1000 mg paracetamol achieves a mean AUC20 of more than 150 min·mg·L$^{-1}$ in fasted healthy human subjects.

In still another embodiment, the present invention provides a method for inducing pain relief including an analgesic effect in a human subject said method comprising administering to said subject a pain relieving effective amount of a swallow formulation comprising a rapidly dissolving form of paracetamol which exhibits a dissolution rate in USP dissolution apparatus 2 using 900 mL of 0.05 N hydrochloric acid at 30 rpm and 37° C. of at least 30% in 180 seconds with a pH modulating agent and an agent which facilitates water uptake into to the tablet, wherein the pH modulating agent is in an amount sufficient to neutralize from about 0.6 mL to about 110 mL 0.1 N hydrochloric acid and/or to neutralize from about 0.06 mmol to about 11 mmol of acid and wherein at least about 70% of the paracetamol in the swallow formulation is dissolved from the swallow formulation within 180 seconds in USP dissolution apparatus 2 with 900 mL 0.05 N hydrochloric acid at 30 rpm and 37° C.

DETAILED DESCRIPTION OF THE PREFERRED EMBODIMENTS

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention provides a paracetamol formulation and in particular a fast dissolving oral dosage form of paracetamol. The oral dosage form is generally referred to herein as a swallow formulation. The swallow formulation generally comprises paracetamol combined with a pH modulating agent and an agent which facilitates uptake of water. The oral dosage form of the present invention may optionally be administered with water or any other aqueous-based fluid.

The present invention provides, therefore, a swallow formulation comprising a rapidly dissolving form of paracetamol, a pH modulating agent and an agent which facilitates water uptake, wherein the pH modulating agent is in an amount sufficient to neutralize from about 0.6 mL to about 110 mL 0.1 N hydrochloric acid and/or to neutralize from about 0.06 mmol to about 11 mmol acid and wherein at least about 70% of the paracetamol in the swallow formulation is dissolved from the swallow formulation within 180 seconds in USP dissolution apparatus 2 with 900 mL 0.05 N hydrochloric acid at 30 rpm and 37° C.

It is to be understood that unless otherwise indicated, the subject invention is not limited to specific formulation components, manufacturing methods, dosage regimens, or the like, and as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "an agent" includes a single agent, as well as two or more agents; reference to "a pH modulating agent" includes a single pH modulating agent, as well as two or more pH modulating agents, reference to "a water uptake agent" includes a single water uptake agent or two or more water uptake agents; and so forth.

The rapidly dissolving form of paracetamol includes a paracetamol having a volume median diameter ($D_{50}$) of less than 350 μm and a surface area of greater than 0.07 m$^2$·g$^{-1}$. Alternatively, or in addition, it includes any paracetamol preparation which exhibits a dissolution rate in USP dissolution apparatus 2 using 900 mL of 0.05 N hydrochloric acid at 30 rpm and 37° C. of at least 30% in 180 seconds.

Accordingly, another aspect of the present invention provides a swallow formulation comprising a form of paracetamol having a volume median diameter ($D_{50}$) of less than 350 μm and a surface area of greater than 0.07 m$^2$·g$^{-1}$; a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake; wherein at least 70% of the paracetamol is dissolved from the swallow formulation within 180 seconds in USP dissolution apparatus 2 with 900 mL 0.05 N hydrochloric acid at 30 rpm and 37° C.

In a related aspect, the present invention is directed to a swallow formulation comprising a form of paracetamol which exhibits a dissolution rate in USP dissolution apparatus 2 using 900 mL of 0.05 N hydrochloric acid at 30 rpm at 37° C. of at least 30% in 180 seconds; a pH modulating agent in an amount sufficient to neutralize from about 0.6 mL to about 110 mL 0.1 N hydrochloric acid and/or to neutralize from about 0.06 mmol to about 11 mmol acid; and an agent which facilitates water uptake, wherein at least 70% of the paracetamol is dissolved from the swallow formulation within 180 seconds in USP dissolution apparatus 2 with 900 mL 0.05 N hydrochloric acid at 30 rpm and 37° C. The swallow formulation of the present invention achieves on administration of 1000 mg paracetamol a mean AUC 20 of more than 150 min·mg·L$^{-1}$ in fasted healthy human subjects.

Accordingly, another aspect of the present invention provides a swallow formulation comprising a form of paracetamol having a volume median diameter ($D_{50}$) of less than 350 μm and a surface area of greater than 0.07 m$^2$·g$^{-1}$; a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake; wherein an administration of 1000 mg paracetamol achieves a mean AUC20 of more than 150 min·mg·L$^{-1}$ in fasted healthy human subjects.

In a related aspect, the present invention provides a swallow formulation comprising a form of paracetamol which exhibits a dissolution rate in USP dissolution apparatus 2 using 900 mL of 0.05 N hydrochloric acid at 30 rpm and 37° C. of at least 30% in 180 seconds; a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake wherein an administration of 1000 mg paracetamol results in a mean AUC20 of more than 150 min·mg·L$^{-1}$ in fasted healthy human subjects.

In describing and claiming the present invention, the following terminology is used in accordance with the definitions set forth below.

The terms "active agent", "compound", "pharmacologically active agent", "medicament", "active", "active ingredient", "drug" and "drug component" are used interchangeably throughout this specification. The terms also encompass pharmaceutically acceptable and pharmacologically active ingredients of those active agents specifically mentioned herein including but not limited to salts, esters, amides, pro-drugs, active metabolites, analogs and the like. When the terms "active agent", "compound", "pharmacologically active agent", "medicament", "active", "drug", "drug component" and "paracetamol" are used, then it is to be understood that this includes those compounds per se as well as pharmaceutically acceptable, pharmacologically active salts, esters, amides, pro-drugs, metabolites, analogs, etc. The terms "agent", "compound" etc may be a single molecule or a composite of molecules.

By the term "effective amount" or "therapeutically effective amount" of paracetamol as used herein means that a sufficient amount of paracetamol is used to provide the desired therapeutic effect or the desired pharmacological, physiological or biochemical event including the amelioration of symptoms being treated or prevented. Of course, undesirable effects, e.g. side effects, are sometimes manifested along with the desired therapeutic effect; hence, a practitioner balances the potential benefits against the potential risks in determining what is an appropriate "effective amount".

The terms "delivery" and "administration" are used interchangeably throughout the specification to mean the act of providing the oral dosage form to an individual. The term "administering" is considered herein synonymous with "delivering", "providing", "introducing" or "swallowing".

By "pharmaceutically acceptable excipient" is meant a pharmaceutical vehicle comprised of a material that is not biologically or otherwise undesirable, i.e. the oral dosage form may be administered to a subject along with paracetamol without causing any or a substantial adverse reaction. Excipients may include carriers and other additives such as diluents, binders, detergents, coloring agents, flavoring agents, wetting or emulsifying agents, preservatives, glidants, lubricants and the like as well as disintegrants.

Similarly, a "pharmacologically acceptable" salt, ester, amide, pro-drug or derivative of paracetamol as provided herein is a salt, ester, amide, pro-drug or derivative that is not biologically or otherwise undesirable.

The terms "treating" and "treatment" as used herein refer to reduction or amelioration in severity and/or frequency of symptoms, elimination of symptoms and/or underlying cause and/or prevention of the occurrence of symptoms and/or their underlying cause. Thus, for example, "treating" a subject involves prevention of a particular disorder or adverse physiological event in a susceptible individual as well as treatment of a clinically symptomatic individual by inhibiting or causing regression of a particular condition. Thus, for example, a method of treating a subject in need of pain relief encompasses both prevention of pain as well as treating conditions of pain. Reference to the treatment of pain includes the induction of analgesia. In addition, the subject formulation is useful for treating the symptoms of conditions requiring pain relief. Conditions contemplated herein include conditions requiring pain and fever management including pain and/or fever relief, pain and/or fever prevention, pain and/or fever reduction and/or treatment of levels of pain and/or fever.

$C_{max}$ is the peak paracetamol plasma concentration. AUC20 is the partial area under the plasma concentration-time curve for 20 minutes after administration. $T_{max}$ is the time to reach peak paracetamol plasma concentration.

Reference to "a pH modulating agent" includes one or more than one pH modulating agents. These may include acids, bases or a combination of one or more acids and/or bases. Reference to more than one includes from 2 to about 10 such as 2, 3, 4, 5, 6, 7, 8, 9 or 10 pH modulating agents.

In one particular embodiment, at least one of the pH modulating agents is soluble and/or dispersible.

In another particular embodiment, at least one of the pH modulating agents is a base.

Non-limiting examples of suitable pH modulating agents include sodium carbonate, ammonium carbonate, sodium bicarbonate, potassium bicarbonate, calcium carbonate, magnesium carbonate, disodium glycine carbonate, sodium glycine carbonate, lysine carbonate, arginine carbonate, citric acid, tartaric acid, malic acid, fumaric acid, metatartaric acid, adipic acid, sodium acid citrate, ascorbic acid and amino acids such as aspartic acid, glutamic acid, glycine, leucine, tyrosine and tryptophan as well as combinations of two or more of the above.

Suitably, at least one of the pH modulating agents is a carbonate such as an alkaline metal carbonate.

Desirably, the carbonate is water soluble.

Preferably the pH modulating agent in the swallow formulation is capable of neutralizing between 12 and 95 mL of 0.1 N HCl. In addition, the pH modulating agent of the swallow formulation is capable of neutralizing between 1.2 and 9.5 mmol of acid.

The pH modulating agent is generally present in an amount form about 2% to about 90% by weight of swallow formulation. More preferably the pH modulating agent is present in an amount from about 2% to about 80%, and most preferably from about 2% to about 70% by weight of swallow formulation. Examples of percentage amounts by weight of pH modulating agent include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90%.

Preferably, the ratio of paracetamol to pH modulating agent is between 0.5:1 and 30:1 inclusive by weight. More preferably, the ratio of paracetamol to pH modulating agent is between 1:1 and 20:1 by weight. Examples including 0.5:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 20:1, 21:1, 22:1, 23:1, 24:1, 25:1, 26:1, 27:1, 28:1, 29:1 or 30:1 by weight.

In one embodiment, the pH modulating agent is sodium bicarbonate and/or potassium bicarbonate and/or magnesium carbonate and/or citric acid and is present in an amount from about 2% to 75% by weight of the swallow formulation.

Paracetamol is conveniently present in an amount of from about 1000 mg or approximately 500 mg per formulation (e. e.g. tablet) and the pH modulating agent is present in an amount from 50 mg to 450 mg per 500 mg of paracetamol such as 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449 or 450 mg per 500 mg formulation.

Preferably, the pH modulating agent is present in an amount from 100 to 300 mg per 500 mg paracetamol in the swallow formulation. Even more preferably the pH modulating agent is sodium bicarbonate.

More preferably the administration of 1000 mg paracetamol in the swallow formulation with water to fasted healthy human subjects provides a mean AUC20 of more than about 170 min·mg·L$^{-1}$ in healthy fasted human subjects.

In one embodiment, the swallow formulation is a tablet and at least 70% of the paracetamol is dissolved from the swallow formulation within 180 seconds in USP dissolution apparatus 2 with 900 mL 0.05 N hydrochloric acid at 30 rpm and 37° C. Even more preferably, at least 80% is dissolved in 180 seconds.

In another embodiment, the swallow formulation is a tablet and at least 70% of the paracetamol is dissolved from the swallow formulation within 120 seconds in USP dissolution apparatus 2 with 900 mL 0.05 N hydrochloric acid at 30 rpm and 37° C. Even more preferably, at least 80% is dissolved in 120 seconds.

In yet another embodiment, the swallow formulation is a tablet and at least 70% of the paracetamol is dissolved from the swallow formulation within 90 seconds in USP dissolution apparatus 2 with 900 mL 0.05 N hydrochloric acid at 30 rpm and 37° C. Even more preferably, at least 80% is dissolved in 90 seconds.

Reference to "paracetamol incorporated in the swallow formulation as a rapidly dissolving form of paracetamol" includes rapidly dissolving forms of paracetamol and any paracetamol which is converted to a rapidly dissolving form of paracetamol during the manufacturing process.

Rapidly dissolving form of paracetamol includes paracetamol having a surface area to mass ratio greater than about 0.08 m$^2$·g$^{-1}$ as measured by gas adsorption and/or paracetamol having a volume median diameter ($D_{50}$) particle size less than about 300 μm as measured by laser diffraction.

In one embodiment, the paracetamol is in a rapidly dissolving form wherein desirably the dissolution rate in USP dissolution apparatus 2 using 900 mL of 0.05 N HCL with the paddle spinning at 30 rpm at 37° C. is at least about 30% in 180 seconds.

Alternatively a standard form of paracetamol may be converted to a rapidly dissolving form during the manufacturing process wherein the finished product will meet a dissolution rate in USP dissolution apparatus 2 using 900 mL of 0.05 N HCL at 30 rpm and 37° C. of at least about 70% in 180 seconds.

In one preferred embodiment, the amount of paracetamol dissolved from the swallow formulation in the presence of a carbonate pH modulating agent is at least 5 times greater than the amount of paracetamol dissolved from a swallow formulation without a carbonate pH modulating agent after 30 seconds in a USP dissolution apparatus 2 with 900 mL 0.05 N hydrochloric acid at 30 rpm and 37° C.

In one embodiment, the rapidly dissolving paracetamol has a $D_{50}$ particle size less than 300 μm.

Rapidly dissolving forms of paracetamol include micro- or sub-micron particles and modified crystals of paracetamol as well as particles having a reduced particle size and/or increased surface area.

In a further embodiment, the rapidly dissolving form of paracetamol is a salt, ester, amide, pro-drug or other pharmaceutically acceptable derivative of paracetamol.

In one embodiment, paracetamol crystals are re-crystallised in the presence of a crystallization modifier such as a polymer or protein or mixtures thereof to produce modified crystals. Polymers which may be used include polyvinlypyrrolidone (PVP) and copolymers with polyvinlypyrrolidone subunits. Proteins which may be used include albumin (bovine or ovine), papain, pepsin and others. Preferably, polyvinlypyrrolidone is present during crystallization.

Preferably the PVP-paracetamol co-crystal has a surface area to mass ratio of greater than 0.2 m$^2$·g$^{-1}$ as measured by gas adsorption.

Conveniently, the modified paracetamol crystals have a $D_{50}$ particle size in the range of 50-300 μm such as 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 or 300 μm.

In one embodiment, the rapidly dissolving form of paracetamol is in the form of granules manufactured by granulation techniques including wet massing, dry slugging or compaction, fluidized bed or spray drying and may include the use of high energy granulators. The granules may also contain a pH modulating agent and/or a water uptake agent. The swallow formulation may optionally contain extra granular paracetamol and/or a pH modulating agent and/or water uptake agent.

Preferably, the granules include one or more disintegrants, such as but not limited to crospovidone, croscarmellose, sodium starch glycolate, starch and/or starch derivatives.

In one embodiment, the rapidly dissolving form of paracetamol is provided in a formulation comprising further molecules which enhance the dissolution of the paracetamol, such as eutectics including mannitol.

Accordingly, another embodiment of the present invention is directed to a swallow formulation comprising paracetamol incorporated as a rapidly dissolving form of paracetamol as described herein and a pH modulating agent wherein the pH modulating agent is in an amount sufficient to neutralize from 0.6 mL to 110 mL 0.1 N hydrochloric acid and which permits at least about 70% of the paracetamol to dissolve from the swallow formulation within 180 seconds in USP dissolution apparatus 2 with 900 mL 0.05 N hydrochloric acid at 30 rpm and 37° C. and which achieves on administration of swallow formulation totalling 1000 mg paracetamol a mean AUC20 of more than 150 min·mg·L$^{-1}$ in fasted healthy human subjects.

The skilled addressee will appreciate, the swallow formulation may also comprise one or more pharmaceutically acceptable excipients.

Reference to "a water uptake agent" includes any agent which will facilitate the uptake of water. These may include wicking agents, disintegrants, binders, carriers and other hydrophilic excipients that will absorb, dissolve in or wick water, used alone or in combination. Generally, but not exclusively, a "water uptake agent" facilitates uptake of water into the swallow formulation.

Suitable water uptake agents include cross-linked polyvinylpyrrolidone (crospovidone), croscarmellose sodium, sodium starch glycolate, starch, starch derivatives, low substituted hydroxypropylcellulose, alginic acid, sodium alginate, calcium sulfate, calcium carboxymethylcellulose, microcrystalline cellulose, powdered cellulose, colloidal silicon dioxide, docusate sodium, guar gum, hydroxypropyl cellulose, magnesium aluminium silicate, methylcellulose, polacrilin potassium, silicified microcrystalline cellulose, magnesium oxide, tragacanth, mannitol, sorbitol, xylitol, sucrose, lactose, fructose, maltose, polyethylene glycol, aminoacids, cyclodextrin, urea and/or polyvinylpyrrolidone (povidone, PVP).

The water uptake agent may be present in an amount from 2% to 80% by weight of the swallow formulation and more preferably between 2% and 60% by weight of the swallow formulation.

Preferably, the ratio of water uptake agent to pH modulating agent is between 0.1:1 and 20:1 by weight such as 0.1:1, 0.2:1, 0.3:1, 0.4:1, 0.5:1, 0.6:1, 0.7:1, 0.8:1, 0.8:1, 0.9:1, 1:1, 2:1, 3:1, 4:1, 5:1, 6:1, 7:1, 8:1, 9:1, 10:1, 11:1, 12:1, 13:1, 14:1 or 15:1, 16:1, 17:1, 18:1; 19:1 and 20:1. More preferably the ratio of water uptake agent to pH modulating agent is between 0.3:1 and 15:1 by weight.

Optionally, the swallow formulation may also comprise one or more pharmaceutically acceptable excipients or other components such as flavoring agents, coloring agents, sweeteners and preservatives.

Accordingly, another aspect of the present invention is directed to a swallow formulation comprising paracetamol incorporated as a rapidly dissolving form of paracetamol as described herein, one or more pH modulating agents wherein the pH modulating agent is in an amount sufficient to neutralize from about 0.6 mL to about 110 mL 0.1 N hydrochloric acid and a water uptake agent in an amount up to 80% by weight of the swallow formulation which permits at least about 70% of the paracetamol to dissolve from the swallow formulation within 180 seconds in USP dissolution apparatus 2 with 900 mL 0.05 N hydrochloric acid at 30 rpm and 37° C. and which achieves on administration of a swallow formulation totalling 1000 mg paracetamol a mean AUC20 of more than 150 min·mg·L$^{-1}$ in fasted healthy human subjects.

In one embodiment, the swallow formulation is co-administered with an aqueous fluid such as water. The co-administered fluid may be administered, before, after or with the swallow formulation.

Accordingly, another aspect of the present invention is directed to a swallow formulation comprising paracetamol incorporated as a rapidly dissolving form of paracetamol as described herein, a water uptake agent and one or more pH modulating agents wherein the pH modulating agent is in an amount sufficient to neutralize from about 0.6 mL to about 110 mL 0.1 N hydrochloric acid and/or to neutralize from about 0.06 mmol to about 11 mmol of acid which permits at least about 70% of the paracetamol to dissolve from the swallow formulation within 180 seconds in USP dissolution apparatus 2 with 900 mL 0.05 N hydrochloric acid at 30 rpm and 37° C. said dosage form further comprising one or more pharmaceutically acceptable carriers, diluents and/or excipients, wherein the swallow formulation is co-administered with fluid.

The paracetamol or salt or pro-active form may be provided from about 100 mg to about 1000 mg per swallow formulation such as 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999 or 1000 mg or a fraction in between. A range of from about 400 to 750 mg is particularly preferred such as from about 450 mg to about 700 mg such as 500 mg or 650 mg per swallow formulation.

The skilled addressee will appreciate the preferred amount of paracetamol will depend upon the intended user of the swallow formulation. For example, in infants under two months of age with post immunization fever 10 to 15 mg paracetamol per kilogram is the recommended dosage. For an adult dose of 1000 mg paracetamol the dose may be administered as a single dose administration comprising one, two, three, four or more swallow formulations. For example, a 1000 mg dose of paracetamol may be administered as a single dose administration of two swallow formulations each containing 500 mg paracetamol, a water uptake agent and pH modulating agent in an amount sufficient to neutralize from about 0.3 mL to about 55 mL 0.1 N hydrochloric acid and/or to neutralize from about 0.03 mmol to about 5.5 mmol of acid.

In one embodiment, the swallow formulation is intended for use by an infant and paracetamol may be in the range of 100 to 250 mg.

In another embodiment, the swallow formulation is intended for use by an adult and paracetamol may be in the range of 250 to 1000 mg.

As indicated above, the most preferred pH modulating agent is sodium bicarbonate and/or calcium carbonate and/or magnesium carbonate and/or potassium bicarbonate which in the swallow formulation is present in from about 25 mg to 450 mg per swallow formulation such as 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 61, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449 or 450 mg.

The swallow formulation may also contain additional pharmaceutically active agents for example other analgesics such as codeine, hydrocodone, oxycodone, tramadol and propoxyphene, anti-inflammatory analgesics such as aspirin and ibuprofen, decongestants such as pseudoephedrine and phenylephrine, antitussives such as pholcodine and dextromethorphan, expectorants such as guaifenesin and bromhexine, non-sedating and sedating antihistamines such as diphenhydramine and chlorpheniramine and muscle relaxants such as doxylamine or salt of these drugs. Formulations may also contain a pharmaceutically acceptable adjuvant such as caffeine.

Accordingly, in one preferred embodiment, the present invention provides a swallow formulation comprising paracetamol incorporated as a rapidly dissolving form of paracetamol as described herein, a water uptake agent and one or more pH modulating agents wherein the pH modulating agent in a dose of paracetamol is in an amount, sufficient to neutralize from about 0.6 mL to about 110 mL 0.1 N hydrochloric acid and/or to neutralize from about 0.06 mmol to about 11 mmol of acid and one or more additional pharmaceutically active ingredients wherein 70% of the paracetamol dissolves from the swallow formulation within 180 seconds in USP dissolution apparatus 2 with 900 mL 0.05 N hydrochloric acid at 30 rpm and 37° C.

Particularly preferred swallow formulations include swallow formulations comprising about 50-65% paracetamol, 21-26% pH modulating agent and about 12-18% water uptake agent by weight of swallow formulation and swallow formulations comprising 50-65% paracetamol, 21-26% sodium bicarbonate, 7-9% crospovidone and 5-7% starch derivative by weight of swallow formulation.

In another aspect of the present invention there is provided a dosage form comprising a swallow formulation comprising paracetamol incorporated as a rapidly dissolving form of paracetamol, a water uptake agent and one or more pH modulating agents wherein the pH modulating agent in a dose of paracetamol is in an amount sufficient to neutralize from about 0.6 mL to about 110 mL 0.1 N hydrochloric acid and/or to neutralize from about 0.06 mmol to about 11 mmol of acid.

The dosage form may be a tablet, capsule, powder, cachet, paste, colloid, gel or melt. The dose form may optionally be in a chewable form.

The dosage form of the present invention may be coated, uncoated and/or layered tablet. Suitable coatings include water soluble polymer based coatings such as, povidone or hypromellose. Suitable coating polymers may also be a derivative of cellulose (cellulose acetophthalate, hypromellose phthalate) or a derivative of an acrylic polymer (methacrylate acid copolymer). Optionally, the dosage form may be coated with gelatin.

The dosage form may contain one or more further pharmaceutically active agents. In one embodiment, the dosage form is a multi phase release dosage form containing a further paracetamol having a dissolution of less than 30% in 180 seconds in USP dissolution apparatus 2 with 900 mL 0.05 N hydrochloric acid at 30 rpm and 37° C.

Swallow formulations of the present invention may be manufactured by admixing the ingredients simultaneously or sequentially and then converting into a dosage unit such as a tablet, capsule, wafer or the like.

Tablets of the present invention may be manufactured by direct compression or granulation and compression for example.

The present invention further contemplates a method for the amelioration of the symptoms of pain, fever or discomfort in a subject, said method comprising administering to said subject a swallow formulation comprising paracetamol incorporated as a rapidly dissolving form of paracetamol as described herein, a water uptake agent and one or more pH modulating agents wherein the pH modulating agent is in an amount sufficient to neutralize from about 0.6 mL to about 110 mL 0.1 N hydrochloric acid and/or to neutralize from about 0.06 mmol to about 11 mmol of acid, the administration being for a time and under conditions to prevent or ameliorate symptoms of the condition.

Another aspect of the present invention contemplates a method for effecting pain and/or fever management in a subject experiencing pain and/or fever or anticipating to experience pain and/or fever, said method comprising administering to said subject a swallow formulation comprising paracetamol incorporated as a rapidly dissolving form of paracetamol as described herein, a water uptake agent and one or more pH modulating agents wherein the pH modulating agent is in an amount sufficient to neutralize from about 0.6 mL to about 110 mL 0.1 N hydrochloric acid and/or to neutralize from about 0.06 mmol to about 11 mmol of acid, the administration being for a time and under conditions to prevent or ameliorate symptoms of the condition.

These methods may also involve the swallow formulation having one or more pharmaceutically acceptable excipients.

EXAMPLES

The present invention is further described by the following non-limiting Examples.
Dissolution Testing In the examples the following USP dissolution apparatus II with 1000 mL dissolution vessels and paddle stirrers was used to perform the dissolution testing:
  VanKel VK 7010 Dissolution bath
  VanKel VK 750 D Heater/Circulator
  Gilson Minipuls peristaltic pump for automatic continuous sampling Testing was conducted using 900 mL of two different dissolution media at 37° C. One was 0.05 N hydrochloric acid. The other was 0.0033 N hydrochloric acid which is effective in discriminating between fast dissolving formulations. 900 mL of this medium contains the absolute amount of acid estimated to be present in the gastric contents in vivo, namely 3 millimoles, and its pH will change when high levels of sodium bicarbonate used in some formulations are added.

The materials used for preparation of dissolution media were:
  32% w/w concentrated hydrochloric acid (HCl) (AR quality from Rowe Scientific)
  RO water from in-house Millipore Elix® water system.

Dissolution results were measured as the mean of 2 replicates. Repeating the testing at 0 rpm provides more discrimination between formulations.

For measurements at 30 rpm, after 20 minutes, the stirring speed was increased to demonstrate the extent of further dissolution that could be achieved.

For measurements at 0 rpm, after 60 minutes, the stirring speed was increased to demonstrate the extent of further dissolution that could be achieved.

In formulations containing paracetamol, paracetamol concentrations were measured using a Varian Cary 50 UV-Vis Spectrophotometer set at an appropriate wavelength. For each drug, the optimal wavelength was selected after running UV scans in the dissolution medium.

For formulations containing paracetamol and tramadol hydrochloride measured at 0 and 30 rpm, the concentrations of each drug were measured by HPLC analysis in 0.75 mL samples taken at 1, 2, 3, 5, 10, 15, 20 and 30 minutes. A final sample was taken at the end of the run after stirring at 250 rpm for 10 minutes to achieve the maximum dissolution Solution pH was measured using a TPS WP81 pH, Salinity, Temperature & Conductivity Meter.

Example 1

Selection of pH Modulating Agents Based on Pharmacokinetic Studies

This non-limiting Example includes a range of different formulations based on rapidly dissolving paracetamol with carbonates as a pH modulating agent over the range 100-800 mg per dose as covered by this invention and the presence of water uptake agents that demonstrate improved tablet dissolution and AUC20 values. Formulation 1 covers the formulation and preparation of paracetamol-PVP crystals which were used as the rapidly dissolving paracetamol in many of the formulations.

All formulations were tested in fasted healthy human subjects, administering two tablets equivalent to a 1000 mg dose of paracetamol with water. Plasma levels of paracetamol were measured for up to 8 hours post-dosing, with at least 10 samples taken during the first hour. In vitro tablet dissolution was measured using USP dissolution apparatus 2 with 900 mL 0.05 N hydrochloric acid at 30 rpm and 37° C.

A linear in vitro-in vivo correlation (IVIVC) ($R^2$=0.60) was established between paracetamol AUC20 and the fitted tablet dissolution exponential rate constant ($k_{diss}$) based on the evaluation of 23 different tablet formulations with each formulation evaluated in 5 subjects in a crossover design. Accordingly, an AUC20 of approximately 150 min·mg·$L^{-1}$ corresponds to about 70% dissolution of paracetamol in 180 sec. A poorer linear correlation existed between $T_{max}$ and $k_{diss}$ for the 23 formulations ($R^2$=0.29). A low $T_{max}$ is generally associated with a high AUC20 but it was found that $T_{max}$ begins to plateau at an AUC20 of approximately 120 min·mg·$L^{-1}$, supporting the use of AUC20 rather than $T_{max}$ as the preferred in vivo measure for rate of absorption.

A validation crossover study of two test and two commercially available formulations in 25 healthy fasted subjects gave a linear correlation between the mean AUC20 and in vitro dissolution rate constant, $k_{diss}$ ($R^2=0.990$). This regression suggests that an AUC20 of 150 min·mg·$L^{-1}$ corresponds to about 70% of paracetamol dissolved from the formulations in 180 sec. The linear correlation between AUC20 and the % paracetamol dissolved at 180 seconds was $R^2=0.996$.

The following tables provide examples of some of the formulations with in vivo pharmacokinetic data and in vitro dissolution performance.

TABLE 1

Formulation 1 For A Rapidly Dissolving Paracetamol

| No | Ingredient | mg/tablet |
|---|---|---|
| 1 | Povidone K-30 (PVP) | 20-45 |
| 2 | Water | — |
| 3 | 96% v/v ethanol | — |
| 4 | Paracetamol | 500 |

Procedure
- A. Prepare a solution of approximately 1% w/w of 1 in 2 in a vessel and cool to 2-5° C.
- B. Heat 3 to around 70° C., keeping the temperature below the boiling point of this flammable solvent, and add sufficient paracetamol to prepare a solution of approximately 35% w/w.
- C. Add B to A in the ratio approximately 1 to 3 by weight
- D. Stir for 5 seconds leaving the mixing vessel on ice.
- E. After 20 minutes, filter the resultant crystals under vacuum and dry at 40° C. to a moisture content of approximately 1%.
- F. Screen through an appropriate sieve (~840 μm).
- G. Assay for paracetamol content.

The quantities of solvents, stirring procedures and settling time prior to filtration need to be determined for each batch size. Different ratios of ethanol and water can be used as solvents for the two phases.

Typically the crystals have a volume median diameter ($D_{50}$) below 300 μm and perform as a rapidly dissolving form of paracetamol.

The resultant crystals typically contain 3-6% PVP, and are assayed for paracetamol content before use. This allows the quantity equivalent to 500 mg paracetamol to be calculated for further processing. The crystals are blended with other ingredients in any formulation before conversion to the finished product, such as by compression to produce a tablet or by filling the powder blend into capsules.

Formulations 2-10 are some of those that were tested in the multiple 5 subject crossover studies to demonstrate the effect of pH modulating agents on the in vitro dissolution and in vivo pharmacokinetic parameters. All are direct compression formulations prepared by blending the ingredients prior to compression.

TABLE 2

Formulations 2-10 Containing Rapidly Dissolving Paracetamol

| | Rapidly Dissolving Paracetamol pH modulating agent | | | | | | | | |
|---|---|---|---|---|---|---|---|---|---|
| | Carbonates including 50-400 mg sodium bicarbonate (100-800 mg per dose) | | | | | | | Non carbonates | None |
| | Formulation Number | | | | | | | | |
| Ingredients | 2 | 3 | 4 | 5 | 6 | 7 | 8 | 9 | 10 |
| Crystals from Formulation 1 equivalent to 500 mg paracetamol | 538 | 538 | 526 | 543 | 0 | 538 | 526 | 526 | 526 |
| Paracetamol, micronised | 0 | 0 | 0 | 0 | 500 | 0 | 0 | 0 | 0 |
| Sodium bicarbonate | 50 | 200 | 200 | 200 | 200 | 400 | 125 | 0 | 0 |
| Potassium bicarbonate | 0 | 0 | 0 | 0 | 0 | 0 | 100 | 0 | 0 |
| Citric acid monohydrate | 6 | 0 | 25 | 25 | 25 | 50 | 0 | 0 | 0 |
| Monohydrogen phosphate | 0 | 0 | 0 | 0 | 0 | 0 | 0 | 200 | 0 |
| Urea | 0 | 0 | 0 | 0 | 0 | 0 | 0 | 30 | 0 |
| Mannitol | 0 | 0 | 0 | 50 | 50 | 0 | 0 | 0 | 0 |
| Starch 1500 | 50 | 50 | 50 | 0 | 0 | 50 | 50 | 50 | 50 |
| Povidone K-30 | 0 | 0 | 0 | 0 | 15 | 0 | 0 | 0 | 0 |
| Crospovidone | 60 | 60 | 60 | 60 | 60 | 60 | 60 | 60 | 60 |
| Stearic acid | 7 | 9 | 9 | 8 | 8 | 11 | 9 | 9 | 6 |

TABLE 3

In Vitro Dissolution and In Vivo Data for Formulations 2-10

| | pH modulating agent | | | | | | | | |
|---|---|---|---|---|---|---|---|---|---|
| | Carbonates including 50-400 mg sodium bicarbonate (100-800 mg per dose) | | | | | | | Non carbonates | None |
| | Mean AUC20 min · mg · L$^{-1}$ (pooled data) | | | | | | | | |
| | 255 | | | | | | | 89 | 144 |
| | Formulation Number | | | | | | | | |
| | 2 | 3 | 4 | 5 | 6 | 7 | 8 | 9 | 10 |
| % released in 90 sec | 92 | 91 | 91 | 96 | 84 | 79 | 75 | 9 | 20 |
| Mean AUC20 min · mg · L$^{-1}$ | 241 | 238 | 256 | 296 | 205 | 309 | 201 | 89 | 144 |
| Mean T$_{max}$ min | 14.4 | 13.3 | 18.3 | 14.4 | 17.7 | 14.9 | 19.5 | 30.2 | 39.6 |

Formulations 11 and 12 are those containing rapidly dissolving paracetamol with pH modulating agent that were evaluated in vivo in 25 healthy fasted subjects compared with two commercially available brands of paracetamol described as "rapid release products".

TABLE 4

Formulation 11 Prepared By Granulation

| No | Ingredient | mg/tablet |
|---|---|---|
| | Part 1 | |
| 1 | Povidone K-29/32 | 20 |
| 2 | Water | |
| 3 | Crospovidone | 10 |
| 4 | Paracetamol, micronised | 500 |
| | Part 2 | |
| 5 | Sodium bicarbonate | 200 |
| 6 | Starch 1500 | 50 |
| 7 | Crospovidone | 60 |
| 8 | Stearic acid | 8 |

Part 1
  A. Prepare a 13% w/w solution of 1 in 2.
  B. Blend 3 and 4.
  C. Spray A onto B in a granulator or mixer to produce a granule suitable for compression.
  D. Dry at 40° C. to a moisture content ~1%.
  E. Screen through a 1,410 μm sieve.
Part 2
  F. Screen 5, 6 and 7 through a 250 μm sieve.
  G. Blend Part 1 with F.
  H. Screen 8 through a 250 μm sieve.
  I. Blend H with G.
  J. Compress.

TABLE 5

Formulation 12 Prepared By Direct Compression

| Item number | Ingredient | mg/tablet |
|---|---|---|
| 1 | Crystals from Formulation 1 equivalent to 500 mg Paracetamol | 519 |
| 2 | Sodium bicarbonate | 200 |
| 3 | Starch 1500 | 50 |
| 4 | Crospovidone | 60 |
| 5 | Stearic acid | 8 |

Procedure
  A. Blend 1, 2, 3 and 4
  B. Blend 5 with A
  C. Compress.

TABLE 6

In Vitro And In Vivo Data For Formulations 11 and 12 Compared With Two Commercially Available Paracetamol Products A and B

| Product | % dissolved in 90 seconds in 900 mL 0.05 N hydrochloric acid | AUC20 min · mg · L$^{-1}$ |
|---|---|---|
| 11 | 81 | 197 |
| 12 | 84 | 207 |
| Commercial Product A | 5 | 80 |
| Commercial Product B | 1 | 100 |

TABLE 5

Formulation 12 Prepared By Direct Compression

| Item number | Ingredient | mg/tablet |
|---|---|---|
| 1 | Crystals from Formulation 1 equivalent to 500 mg Paracetamol | 519 |
| 2 | Sodium bicarbonate | 200 |
| 3 | Starch 1500 | 50 |
| 4 | Crospovidone | 60 |
| 5 | Stearic acid | 8 |

Procedure
  A. Blend 1, 2, 3 and 4
  B. Blend 5 with A
  C. Compress.

TABLE 6

In Vitro And In Vivo Data For Formulations 11 and 12 Compared
With Two Commercially Available Paracetamol Products A and B

| Product | % dissolved in 90 seconds in 900 mL 0.05 N hydrochloric acid | AUC20 min · mg · L$^{-1}$ |
|---|---|---|
| 11 | 81 | 197 |
| 12 | 84 | 207 |
| Commercial Product A | 5 | 80 |
| Commercial Product B | 1 | 100 |

Example 2

Selection of Rapidly Dissolving Paracetamol

The following data demonstrate the effect of the addition of a pH modulating agent, sodium bicarbonate, on the in vitro dissolution of tablets made with different grades of paracetamol. Six different grades of paracetamol were tested in Formulations 13-18. For each sample of paracetamol, two formulations were prepared; one without pH modulating agent designated A, and one with pH modulating agent designated B.

TABLE 7

Formulations A and B

| Item number | Ingredient | mg/tablet | |
|---|---|---|---|
| | | Formulation A | Formulation B |
| 1 | Paracetamol | 100 | 100 |
| 2 | Sodium bicarbonate | 0 | 100 |
| 3 | Microcrystalline cellulose | 270 | 270 |
| 4 | Crospovidone | 25 | 25 |
| 5 | Magnesium stearate | 5 | 5 |

Procedure

A. Blend 1, 2, 3 and 4
B. Blend 5 with A
C. Compress.

In vitro dissolution was measured using USP dissolution apparatus 2 with 900 mL 0.05 N hydrochloric acid at 30 rpm and 37° C. The % paracetamol dissolved at 30 seconds was compared for each grade of paracetamol with and without the presence of a pH modulating agent, sodium bicarbonate. The % increase in dissolution caused by the sodium bicarbonate was calculated. It was found that the increase in dissolution caused by sodium bicarbonate is much higher for certain grades of paracetamol. For the purposes of this invention, where the increase is greater than 500%, these grades of paracetamol are described as rapidly dissolving paracetamol. Paracetamol used in Formulations 13-16 meet the definition of rapidly dissolving paracetamol and those used in Formulations 17-18 do not.

TABLE 8

The Effect Of Paracetamol Grade On Dissolution Of Tablets
Formulated With And Without Sodium Bicarbonate

| Paracetamol Sample Formulation Number | Volume Median Diameter ($D_{50}$) μm | Surface Area by argon m$^2$ · g$^{-1}$ | % paracetamol dissolved after 30 sec | | % Increase with Sodium Bicarbonate B/A × 100 |
|---|---|---|---|---|---|
| | | | Without Sodium Bicarbonate A | With 100 mg Sodium Bicarbonate B | |
| 13 | 17  | 0.661 | 4.71 | 45.26 | 961 |
| 14 | 65  | 0.260 | 1.83 | 21.01 | 1148 |
| 15 | 203 | 0.365 | 2.36 | 32.84 | 1392 |
| 16 | 232 | 0.091 | 1.76 | 17.28 | 982 |
| 17 | 398 | 0.063 | 0.46 | 0.72  | 157 |
| 18 | 412 | 0.057 | 1.19 | 0.92  | 77 |

Example 3

Selection of Range of Water Uptake Agents Based on In Vitro Dissolution Studies

Various excipients used in the formulations can be generally classified as water uptake agents in addition to their specific categorization as disintegrants, wicking agents, binders and fillers. Microcrystalline cellulose is an example that can be described in all these categories. For the purposes of this invention, any excipients which are described in any of these categories are considered under the definition of water uptake agent.

It was found that in vitro dissolution did not occur rapidly unless there was sufficient water uptake agent present in combination with the pH modulating agent. It was further noted that a reduction in the in vitro dissolution of tablets was associated with an increase in the level of pH modulating agent, and that the dissolution performance could be restored by increasing the level of water uptake agent. Formulation 10 which contains water uptake agents but without any pH modulating agent shows slow dissolution of paracetamol reaching only 20% in 180 seconds. This compares with dissolution above 70% in 90 seconds when sufficient of both agents are present in the formulation.

The % of water uptake agents in the tablet and the ratio of the water uptake agents to the weight of pH modulating agents are important to achieve the target in vitro dissolution performance of the resultant tablet.

TABLE 9

Formulations With Dissolution Greater Than 70% In 180 Seconds Containing Different Water Uptake Agents

| Item No | Ingredient | mg/tablet Formulation Number | | | | |
|---|---|---|---|---|---|---|
| | | 19 | 20 | 21 | 22 | 23 |
| 1 | Paracetamol, micronised | 500 | 500 | 500 | 100 | 100 |
| 2 | Sodium bicarbonate | 275 | 275 | 275 | 100 | 40 |
| 3 | Microcrystalline cellulose | 0 | 0 | 0 | 270 | 0 |
| 4 | Povidone K-30 | 0 | 0 | 0 | 0 | 4 |
| 5 | Starch 1500 | 70 | 70 | 70 | 0 | 10 |
| 6 | Croscarmellose | 0 | 67 | 0 | 0 | 0 |
| 7 | Sodium starch glycolate | 0 | 0 | 67 | 0 | 0 |
| 8 | Crospovidone | 67 | 0 | 0 | 0 | 12 |
| 9 | Stearic acid | 7 | 7 | 7 | 0 | 0 |
| 10 | Magnesium stearate | 0 | 0 | 0 | 5 | 1 |

Procedure
A. Blend items 1-8 according to the specific formulation
B. Blend item 9 or 10 with A according to the specific formulation
C. Compress.

Examples 4 & 5

The present invention is further described by the following additional non-limiting examples which relate to products containing paracetamol which are prepared by wet granulation and demonstrate fast in vitro dissolution of the active ingredients under the test conditions described:
Example 4: Paracetamol 500 mg tablets
Example 5: Paracetamol 325 mg with tramadol hydrochloride 37.5 mg
Both examples contain dissolution profiles for:
one formulation according to the invention with bicarbonate alone designated 1
a second formulation according to the invention containing sodium bicarbonate with fumaric acid as an example of an organic acid designated 2
a commercial product which contains no pH modulating agents as well as any fast dissolving commercial products containing pH modulating agents For these examples, dissolution data are provided using different dissolution media and stirring conditions in USP dissolution apparatus 2 at 37° C. The additional methods using 0.0033 N hydrochloric acid at 30 rpm and 0 rpm discriminate better between formulations designed for fast dissolution than the 0.05 N hydrochloric acid where the effect of the high acid concentration tends to mask formulation effects on dissolution.

In 900 mL 0.0033 N hydrochloric acid, there is 3 millimoles of acid, approximating the amount of acid estimated to be present in the residual gastric contents in a fasted subject. This amount of acid can be completely neutralized by high amounts of bases used as pH modulating agents, so that the pH of the dissolution medium will change depending on the levels of pH modulating agents used in a formulation. This is particularly important for investigating the dissolution of drugs where their solubility is pH dependent. For example, tramadol hydrochloride is the salt of a base, and its solubility is reduced as the pH increases, whereas the solubility of paracetamol is independent of the pH.

Dissolution results using 900 mL 0.0033 N hydrochloric acid may be of importance in vivo as the acidity of gastric contents varies significantly, and low acid conditions are associated with the fed and partial prandial states, as well as in patients with suppressed gastric function. Further analysis of data from the trial on the rapidly absorbed paracetamol tablets in 25 healthy fasted human subjects carried out by the applicant, established an in vitro in vivo correlation (IVIVC) between the AUC10 ($R^2$=0.91) and AUC20 ($R^2$=0.87) for paracetamol and the in vitro % drug dissolved in 300 seconds in USP apparatus 2 with 900 mL 0.0033 N hydrochloric acid at 30 rpm and 37° C.

When the stirring speed is reduced to 0 rpm, the dissolution profiles demonstrate the intrinsic characteristics of the fast dissolving formulations of this invention which are able to enhance the dissolution of the drugs without any external stirring. Dissolution results without stirring may be of in vivo significance in conditions where there is gut stasis or reduced gastric activity.

For the dissolution profiles for paracetamol alone, drug concentrations were measured by UV absorbance at an appropriate wavelength for each drug using flow through cells for automatic continuous sampling.

For the paracetamol/tramadol dissolution profiles, drug concentrations were measured by HPLC analysis for each drug in samples taken at selected intervals.

Overview of Examples and Methods of Preparation

Example 4 covers paracetamol tablet formulations manufactured by a granulation process containing either sodium bicarbonate alone as the only pH modulating agent, or a combination of sodium bicarbonate and fumaric acid. These are compared with two commercial fast dissolving paracetamol products, Product X from the USA, and Product Y which contains 630 mg sodium bicarbonate as a pH modulating agent from Australia.

Example 5 covers tablet formulations manufactured by a granulation process containing paracetamol with the hydrochloride salt of a base analgesic drug, tramadol hydrochloride. One contains sodium bicarbonate alone as the pH modulating agent, and the other a combination of sodium bicarbonate and fumaric acid. These are compared with a commercial product sourced from the USA containing the same doses of paracetamol and tramadol hydrochloride.

Overview of Results

Tables 10-12 summarise the percentages of the total dose of the drug dissolved for the two examples under different dissolution conditions, namely 900 mL 0.05 N hydrochloric acid at 30 rpm, 900 mL 0.0033 N hydrochloric acid at 30 rpm and 900 mL 0.0033 N hydrochloric acid at 0 rpm respectively. These include dissolution data for commercially available products.

Table 13 details the formulations for the two paracetamol formulations A1 and A2 of Example 4.

Tables 14-16 summarise the paracetamol dissolution data for the two formulations compared with the two commercial products, X and Y under the different dissolution conditions, namely 900 mL 0.05 N hydrochloric acid at 30 rpm, 900 mL 0.0033 N hydrochloric acid at 30 rpm and 900 mL 0.0033 N hydrochloric acid at 0 rpm.

Table 17 details the formulations for the two paracetamol with tramadol hydrochloride formulations, B1 and B2 of Example 5.

Table 18 summarises the dissolution data for paracetamol and tramadol hydrochloride from B1 and B2 compared with a commercial product, in 900 mL 0.05 N hydrochloric acid at 30 rpm.

Table 19 summarises the dissolution data for paracetamol and tramadol hydrochloride from B1 and B2 compared with a commercial product in 900 mL 0.0033 N hydrochloric acid at 30 rpm.

Table 20 summarises the dissolution data for paracetamol and tramadol hydrochloride from B1 and B2 in 900 mL 0.0033 N hydrochloric acid at 0 rpm.

FIGS. 1-3 illustrate the paracetamol dissolution profiles for the two formulations compared with Products X and Y under different dissolution conditions, namely 900 mL 0.05 N hydrochloric acid at 30 rpm, 900 mL 0.0033 N hydrochloric acid at 30 rpm and 900 mL 0.0033 N hydrochloric acid at 0 rpm respectively.

FIG. 4 illustrates the dissolution profiles for paracetamol and tramadol hydrochloride from B1 and B2 compared with a commercial product in 900 mL 0.05 N hydrochloric acid at 30 rpm, FIG. 5 illustrates the dissolution profiles for paracetamol and tramadol ydrochloride from B1 and B2 compared with a commercial product in 900 mL 0.0033 N hydrochloric acid at 30 rpm.

FIG. 6 illustrates the dissolution profiles for paracetamol and tramadol hydrochloride from B1 and B2 in 900 mL 0.0033 N hydrochloric acid at 0 rpm.

CONCLUSIONS AND FURTHER COMMENTS BASED ON EXAMPLES 4 & 5

It will be apparent that the use of pH modulating agents in accordance with the current invention substantially increases the in vitro dissolution of the active ingredients from formulations containing paracetamol alone and in combination with other drugs such tramadol hydrochloride.

However, when paracetamol is used in combination with a base such as tramadol hydrochloride, it is found that the fastest in vitro dissolution of both drugs is achieved by using a bicarbonate with an organic acid compared with a bicarbonate alone. This combination of pH modulating agents provides intrinsic micro-stirring than will enhance the rate of dissolution of both drugs to a greater extent than the use of a base alone. Formulation B2 which contains an a pH modulating comprising an acid and a base at 19% w/w has a greater effect enhancing dissolution compared with B1 which contains 28% w/w of bicarbonate alone.

The in vitro dissolution results in 0.0033 N hydrochloric acid identify formulation differences that are not apparent when the more concentrated acid at 0.05 N hydrochloric acid is used. At 0 rpm, the effect of the intrinsic micro-stirring in the formulation is apparent.

Table 10 summarises dissolution data for formulation examples containing paracetamol alone (A), and paracetamol with tramadol hydrochloride (B) that demonstrate the current invention in 900 mL 0.05 N hydrochloric acid using USP apparatus 2 at 30 rpm and 37° C.:

TABLE 10

Dissolution profiles for formulations according to the invention at 30 rpm stirring speed in 900 mL 0.05 N hydrochloric acid

| Drug | Example | % dissolved in 900 mL 0.05 N hydrochloric acid at 30 rpm | | |
|---|---|---|---|---|
| | | 120 sec | 180 sec | 300 sec |
| Paracetamol | A1 (base alone) | 93 | 94 | 94 |
| | A2 (base + acid) | 92 | 99 | 99 |
| | Product X | 9 | 18 | 32 |

TABLE 10-continued

Dissolution profiles for formulations according to the invention at 30 rpm stirring speed in 900 mL 0.05 N hydrochloric acid

| Drug | Example | % dissolved in 900 mL 0.05 N hydrochloric acid at 30 rpm | | |
|---|---|---|---|---|
| | | 120 sec | 180 sec | 300 sec |
| | Product Y (base) | 5 | 26 | 80 |
| | B1 (base alone) | 52 | 54 | 55 |
| | B2 (base + acid) | 92 | 95 | 98 |
| | Commercial Product | 0 | 1 | 7 |
| Tramadol hydrochloride | B1 (base alone) | 66 | 68 | 68 |
| | B2 (base + acid) | 87 | 93 | 97 |
| | Commercial Product | 2 | 3 | 7 |

These results show that for a combination product of paracetamol with a salt of a basic drug, pH modulating agents comprising an acid and a base are required to achieve more than 70% dissolution of both drugs after 180 seconds at 30 rpm in 0.05 N hydrochloric acid. For paracetamol alone, a base alone is sufficient to achieve this rate of dissolution.

Table 11 summarises the dissolution data for formulation examples containing paracetamol alone (A), and paracetamol with tramadol hydrochloride (B) that demonstrate the current invention in 900 mL 0.0033 N hydrochloric acid using USP apparatus 2 at 30 rpm and 37° C.:

TABLE 11

Dissolution profiles for paracetamol and tramadol hydrochloride in formulations according to the invention at 30 rpm stirring speed in 900 mL 0.0033 N hydrochloric acid

| Drug | Example | % dissolved in 900 mL 0.0033 N hydrochloric acid at 30 rpm | | |
|---|---|---|---|---|
| | | 120 sec | 180 sec | 300 sec |
| Paracetamol | A1 (base alone) | 49 | 60 | 69 |
| | A2 (base + acid) | 71 | 73 | 78 |
| | Product X | 7 | 16 | 30 |
| | Product Y (base) | 3 | 10 | 25 |
| | B1 (base alone) | 9 | 15 | 25 |
| | B2 (base + acid) | 89 | 90 | 91 |
| | Commercial Product | 1 | 4 | 12 |
| Tramadol hydrochloride | B1 (base alone) | 17 | 32 | 55 |
| | B2 (base + acid) | 101 | 102 | 102 |
| | Commercial Product | 3 | 6 | 10 |

These results in more dilute acid, show the enhanced dissolution of both paracetamol and tramadol hydrochloride from combination products when the pH modulating agent comprises a base and an acid. Only when the pH modulating agent comprises an acid and a base does the dissolution achieve greater than 70% in 180 seconds in this less acidic dissolution medium.

Table 12 summarises the dissolution data for formulation examples containing paracetamol alone (A), and paracetamol with tramadol hydrochloride (B) that demonstrate the current invention in 900 mL 0.0033 N hydrochloric acid using USP apparatus 2 at 0 rpm and 37° C.:

TABLE 12

Dissolution profiles in formulations according to the invention at 0 rpm stirring speed in 900 mL 0.0033 N hydrochloric acid

| Drug | Example | % dissolved in 900 mL 0.0033 N hydrochloric acid at 0 rpm | | | |
|---|---|---|---|---|---|
| | | 180 sec | 300 sec | 15 min | 30 min |
| Paracetamol | A1 (base alone) | 3 | 6 | 8 | 12 |
| | A2 (base + acid) | 37 | 42 | 50 | 55 |
| | Product X | 1 | 1 | 3 | 10 |
| | Product Y (base) | 0 | 1 | 3 | 4 |
| | B1 (base alone) | 1 | 2 | 7 | 13 |
| | B2 (base + acid) | 83 | 90 | 94 | 101 |
| Tramadol hydrochloride | B1 (base alone) | 1 | 2 | 10 | 25 |
| | B2 (base + acid) | 93 | 99 | 101 | 103 |

It will be apparent that the use of pH modulating agents in accordance with the current invention substantially increases in vitro dissolution of the therapeutic agents exemplified under conditions without stirring (0 rpm) that highlight the role of micro-stirring in enhancing dissolution.

It is clear from these results that all formulations containing an acid and a base according to the invention had:

a dissolution rate greater than 70% at 180 seconds at 30 rpm in 900 mL 0.05 N hydrochloric acid a dissolution rate greater than 70% at 180 seconds at 30 rpm in 900 mL 0.0033 N hydrochloric acid where a dissolution rate greater than 5% at 30 minutes at 0 rpm in 900 mL 0.0033 N hydrochloric acid.

Formulations that contain a base alone and do not demonstrate these rates of dissolution are considered sub-optimal and would be reformulated to optimise the pH modulating agent for maximum dissolution.

Example 4

Paracetamol

TABLE 13

Paracetamol Formulations

| Item | Formulation | A1 (base alone) | A2 (base + acid) |
|---|---|---|---|
| 1 | Paracetamol (mg) | 500 | 500 |
| 2 | Crospovidone (mg) | 40 | 40 |
| 3 | Sodium bicarbonate (mg) | 200 | 200 |
| 4 | Fumaric acid (mg) | 0 | 34 |
| 5 | Starch 1500 (mg) | 50 | 50 |
| 6 | Povidone (mg) | 34.4 | 40 |
| 7 | Water | 200 | 0 |
| 8 | Ethanol | 0 | 125 |
| 9 | Crospovidone (mg) | 60 | 60 |
| 10 | Stearic acid | 9 | 9 |
| Total tablet weight (mg) | | 893.4 | 933 |
| pH modulating agent (%) | | 22.4 | 25.1 |
| Hardness (Kp) | | 10 | 17 |
| Disintegration Time in 0.05 N hydrochloric acid (Sec) | | 24 | 28 |

Method for Formulation A1

Part 1

A. Prepare a solution of 6 in 7.

B. Blend items 1, 2 and 5.

C. Spray A onto B in a granulator or mixer to form a granule suitable for compression.

D. Dry at 70° C. inlet temperature in a fluid bed dryer to a loss on drying of ~1% after heating at 100° C. for 5 minutes.

E. Screen through a 1000 μm sieve.

Part 2

F. Screen items 3, 9 through a 280 μm sieve.

G. Blend Part 1 with F.

H. Screen item 10 through a 280 μm sieve.

I. Blend G with H.

J. Compress using 19 mm×9 mm oval shallow concave tooling with a break bar on one face to suitable hardness and disintegration time.

Method for Formulation A2

Part 1

A. Blend items 1 to 5.

B. Prepare solution of 6 in 8.

C. Spray B onto A in a granulator or mixer to form a granule suitable for compression.

D. Dry at 40° C. to a loss on drying of <1% after heating at 50° C. for 20 min.

E. Screen through a 500 μm sieve.

Part 2

F. Screen item 9 through a 280 μm sieve.

G. Blend Part 1 with F.

H. Screen item 10 through a 280 μm sieve.

I. Blend G with H.

J. Compress using 19 mm×9 mm oval shallow concave tooling with a break bar on one face to suitable hardness and disintegration time.

Dissolution Results

For 900 mL 0.05 N acid at 30 rpm, dissolution data are summarised in Table 14 and the dissolution profiles are presented in FIG. 1

TABLE 14

Paracetamol Dissolution in 900 mL 0.05 N hydrochloric acid at 30 rpm

| Formulation | % drug dissolved in 900 mL 0.05 N hydrochloric acid at 30 rpm | | | |
|---|---|---|---|---|
| | A1 (base alone) | A2 (base + acid) | Product X | Product Y (base) |
| 120 sec | 93 | 92 | 9 | 5 |
| 180 sec | 94 | 98 | 18 | 26 |
| 240 sec | 94 | 99 | 26 | 57 |
| 300 sec | 94 | 99 | 32 | 80 |

Both paracetamol formulations demonstrate similar fast dissolution profiles, superior to both commercial products. The commercial product containing the sodium bicarbonate demonstrates faster dissolution than the commercial product without a base since the bicarbonate reacts with the high concentration of acid in the dissolution medium, and the resultant effervescence enhances dissolution.

For 900 mL 0.0033 N hydrochloric acid at 30 rpm, dissolution data are summarised in Table 15 and the dissolution profiles are presented in FIG. 2.

TABLE 15

Paracetamol Dissolution in 900 mL 0.0033
N hydrochloric acid at 30 rpm

% drug dissolved in 900 mL 0.0033 N hydrochloric acid at 30 rpm

| Formulation | A1 (base alone) | A2 (base + acid) | Product X | Product Y (base) |
|---|---|---|---|---|
| 180 sec | 60 | 73 | 16 | 10 |
| 300 sec | 69 | 78 | 30 | 25 |
| 15 min | 85 | 91 | 61 | 57 |
| 30 min | 98 | 102 | 77 | 76 |
| Final pH | 3.0 | 2.9 | 2.3 | 6.6 |

The faster dissolution of the formulation with base and acid becomes apparent compared with the use of base alone. Both formulations are faster than the two commercial products, but in this weaker acid, the dissolution profile for the commercial product containing sodium bicarbonate is similar to that for the commercial product without any pH modulating agents.

At this lower acid concentration, the effect of the formulations per se in enhancing dissolution are becoming apparent and the pH change seen with the high level of sodium bicarbonate in Product Y is evident, increasing the pH to 6.6. In the weaker acid, the dissolution of formulation A2 containing both base and acid is faster than for the formulation A1 with base alone. In the latter case, formulation A1 is dependent on external acid for the micro-stirring to enhance dissolution. When the higher concentration of acid is used at 0.05 N, the vigorous reaction with any basic components in the formulations appears to mask any formulation effects.

For 900 mL 0.0033 N hydrochloric acid at 0 rpm, dissolution data are summarised in Table 16 and the dissolution profiles are presented in FIG. 3.

TABLE 16

Paracetamol Dissolution in 900 mL 0.0033
N hydrochloric acid at 0 rpm

% drug dissolved in 900 mL 0.0033 N hydrochloric acid at 0 rpm

| Formulation | A1 (base alone) | A2 (base + acid) | Product X | Product Y (base) |
|---|---|---|---|---|
| 180 sec | 3 | 37 | 1 | 0 |
| 300 sec | 6 | 42 | 1 | 1 |
| 15 min | 8 | 50 | 3 | 3 |
| 30 min | 12 | 55 | 10 | 4 |
| Final pH | 3.0 | 2.9 | 2.3 | 6.6 |

The intrinsic effect of the formulations in enhancing dissolution becomes apparent as the effect of the external acidity in the dissolution medium is reduced and external stirring is eliminated. Under these conditions, only formulation A2 containing the base and acid continues to demonstrate fast and significant levels of dissolution. However the dissolution from formulation A1 is still faster over the first 20 minutes than the two commercial products, particularly product Y containing sodium bicarbonate.

Example 5
Paracetamol and Tramadol Hydrochloride

TABLE 17

Paracetamol and Tramadol Hydrochloride Formulations

| Item | Formulation | B1 (base alone) | B2 (base + acid) |
|---|---|---|---|
| 1 | Paracetamol (mg) | 325 | 162.5 |
| 2 | Sodium bicarbonate (mg) | 200 | 100 |
| 3 | Crospovidone (mg) | 10 | 12.5 |
| 4 | Povidone (mg) | 0 | 8.4 |
| 5 | Water (mg) | 0 | 50 |
| 6 | Paracetamol (mg) | 0 | 162.5 |
| 7 | Tramadol Hydrochloride (mg) | 37.5 | 37.5 |
| 8 | Fumaric acid (mg) | 0 | 34 |
| 9 | Microcrystalline cellulose (mg) | 0 | 50 |
| 10 | Crospovidone (mg) | 0 | 12.5 |
| 11 | Povidone (mg) | 13.67 | 5 |
| 12 | Water (mg) | 55 | 33 |
| 13 | Prosolve (mg) | 50 | 0 |
| 14 | Microcrystalline cellulose (mg) | 0 | 50 |
| 15 | Crospovidone (mg) | 60 | 60 |
| 16 | Magnesium stearate (mg) | 0 | 7 |
| 17 | Steric acid (mg) | 8 | 0 |
| | Total tablet weight (mg) | 704.17 | 701.9 |
| | pH modulating agent (%) | 28.4 | 19.1 |
| | Hardness (Kp) | 14 | 10 |
| | Disintegration Time in 0.05 N hydrochloric acid (Sec) | 16 | 20 |

Method for Formulation B1
Part 1
    A. Prepare a solution of 11 in 12.
    B. Blend items 1, 3, and 7.
    C. Spray A onto B in a granulator or mixer to form a granule suitable for compression.
    D. Dry at 50° C. to achieve moisture content <1%.
Part 2
    E. Screen granules from D through a 1,000 μm sieve.
    F. Screen items 2, 13 and 15 through a 280 μm sieve.
    G. Blend E with F.
    H. Screen item 17 through a 280 μm sieve.
    I. Blend G with H.
    J. Compress using 19 mm×7 mm oval shallow concave tooling with a break bar on one face to suitable hardness and disintegration time.

Method for Formulation B2
Part 1
    A. Prepare a solution of 1 in 12.
    B. Blend items 6, 7, 8, 9 and 10.
    C. Spray A onto B in a granulator or mixer to form a granule suitable for compression.
    D. Dry at 70° C. inlet temperature in a fluid bed dryer to a loss on drying of ~1% after heating at 50° C. for 20 minutes.
Part 2
    E. Prepare a solution of 4 in 5.
    F. Blend items 1, 2 and 3.
    G. Spray A onto B in a granulator or mixer to form a granule suitable for compression.
    H. Dry at 70° C. inlet temperature in a fluid bed dryer to a loss on drying of <1% after heating at 50° C. for 20 minutes.
Part 3
    I. Screen granules from steps D & H through a 500 μm sieve.
    J. Screen items 14 and 15 through a 280 μm sieve.
    K. Blend Part I with J.
    L. Screen item 16 through a 280 μm sieve.
    M. Blend K with L.
    N. Compress using 19 mm×7 mm oval shallow concave tooling with a break bar on one face to suitable hardness and disintegration time.

Dissolution Results

In 900 mL 0.05 N acid at 30 rpm, both formulations demonstrate fast dissolution profiles for both drugs, superior to the commercial product which demonstrates a gradual increase in dissolution. The formulation with base and acid (B2) reaches 100% within 5 minutes for both paracetamol and tramadol. However, while the formulation with base alone (B1), shows fast dissolution for tramadol, it shows slower dissolution for the paracetamol, even though the level of pH modulating agent is higher at 28%, Tramadol hydrochloride is more soluble than paracetamol with a solubility in water around 30 mg/mL compared with 14 mg/mL for paracetamol. On a weight for weight basis, the tramadol hydrochloride needs around 1 mL for total dissolution compared to around 27 mL for the dose of paracetamol.

These results suggest a synergistic effect of the base and acid together, achieving improved dissolution at a lower level of pH modulating agent. The intrinsic micro-stirring in the tablet appears to be more effective in promoting the dissolution of the lesser soluble drug compared with the mixing achieved as a result of the reaction between the base and the acid in the dissolution medium.

TABLE 18

Paracetamol and Tramadol Hydrochloride Dissolution in 900 mL 0.05 N hydrochloric acid at 30 rpm % drug dissolved in 900 mL 0.05 N hydrochloric acid at 30 rpm

| Formulation | B1 (base alone) | | B2 (base + acid) | | Commercial Product | |
|---|---|---|---|---|---|---|
| | Paracetamol | Tramadol | Paracetamol | Tramadol | Paracetamol | Tramadol |
| 120 sec | 66 | 86 | 92 | 87 | 0 | 2 |
| 180 sec | 67 | 88 | 95 | 93 | 1 | 3 |
| 300 sec | 69 | 88 | 98 | 97 | 7 | 7 |
| 15 min | 74 | 91 | 98 | 97 | 53 | 36 |
| 30 min | 80 | 93 | 98 | 97 | 87 | 80 |
| Final pH | 1.1 | | 1.1 | | 1.1 | |

In 900 mL 0.0033 N hydrochloric acid at 30 rpm, only the formulation with base and acid (B2) demonstrates very fast dissolution reaching 100% within 5 minutes.

The formulation with the higher level of bicarbonate alone (28%) shows slower dissolution for both drugs although again, the dissolution of the more soluble tramadol hydrochloride is faster than that of the paracetamol. Dissolution of this formulation does not show significantly improved dissolution compared with the commercial product.

TABLE 19

Paracetamol and Tramadol Hydrochloride Dissolution in 900 mL 0.0033 N hydrochloric acid at 30 rpm % drug dissolved in 900 mL 0.0033 N hydrochloric acid at 30 rpm

| Formulation | B1 (base alone) | | B2 (base + acid) | | Commercial Product | |
|---|---|---|---|---|---|---|
| | Paracetamol | Tramadol | Paracetamol | Tramadol | Paracetamol | Tramadol |
| 120 sec | 6 | 13 | 89 | 101 | 1 | 3 |
| 180 sec | 11 | 23 | 90 | 102 | 4 | 6 |
| 300 sec | 19 | 40 | 91 | 102 | 12 | 10 |
| 15 min | 39 | 69 | 92 | 103 | 60 | 51 |
| 30 min | 56 | 83 | 94 | 103 | 89 | 95 |
| Final pH | 2.5 | | 2.4 | | 2.2 | |

In 900 mL 0.0033 N hydrochloric acid at 0 rpm, the intrinsic dissolution enhancing features of the formulations become apparent as the effect of the external acidity is reduced and external stirring is eliminated. Under these conditions, formulation B2 containing the base and acid demonstrates fast and significant levels of dissolution compared with the formulation with base alone.

TABLE 20

Paracetamol and Tramadol Hydrochloride Dissolution in 900 mL 0.0033 N hydrochloric acid at 0 rpm % drug dissolved in 900 mL 0.0033 N hydrochloric acid at 0 rpm

| Formulation | B1 (base alone) | | B2 (base + acid) | |
|---|---|---|---|---|
| | Paracetamol | Tramadol | Paracetamol | Tramadol |
| 120 sec | 1 | 1 | 78 | 86 |
| 180 sec | 1 | 1 | 83 | 93 |
| 300 sec | 2 | 3 | 85 | 96 |
| 15 min | 7 | 10 | 94 | 101 |

TABLE 20-continued

Paracetamol and Tramadol Hydrochloride Dissolution
in 900 mL 0.0033 N hydrochloric acid at 0 rpm

| | % drug dissolved in 900 mL 0.0033 N hydrochloric acid at 0 rpm | | | |
|---|---|---|---|---|
| | B1 (base alone) | | B2 (base + acid) | |
| Formulation | Paracetamol | Tramadol | Paracetamol | Tramadol |
| 30 min | 13 | 25 | 101 | 103 |
| Final pH | 2.8 | | 2.5 | |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Ameer et al., *J. Pharm. Sci,* 72:955-958, 1983
Chen et al, *Clin. Pharmacokinet.* 40(8):565-72, 2001
Grattan et al, *Eur. J. Pharm. Biopharm.* 49 (3):225-229, 2000
FDA Guidance for Industry, Bioavailability & Bioequivalence Studies for Orally Administered Drug Products—General Considerations, March 2003
Luthy, et al. *Schweiz Med. Wochenschr* 123 (Suppl 50)/II:406, 1993
McNeil Consumer & Speciality Pharmaceuticals, Submission to the FDA on acetaminophen for 19 Sep. 2002 Nonprescription Drugs Advisory Committee Meeting.
Nielsen et al. *Eur. J. Clin. Pharmacol.* 42(3): 261-264, 1992
Prescott, *Medical Clinics oj 'North America,* 58:907-916, 1974
Prescott, *Am. J. Ther.* 7(2): 143 -147 2000
Rumble et al, *Clin. Pharmacokinet.* 20 (2): 167-173, 1991
Rumack et al, *Pediatrics* 62 (Suppl): 898-903, 1978
US Patent Application No. 20040170681
US Patent Application No. 20040204475
U.S. Pat. No. 6,316,025

The invention claimed is:

1. A swallow formulation comprising paracetamol particles having a volume median diameter ($D_{50}$) of less than 350 µm and a surface area of greater than 0.07 $m^2 g^{-1}$, a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake into the formulation; wherein at least 70% of the paracetamol is dissolved from the swallow formulation within 180 seconds in USP dissolution apparatus 2 with 900 mL 0.05 N hydrochloric acid at 30 rpm and 37° C., wherein the weight ratio of the paracetamol and the pH modulating agent is between 1.8:1 and 2.5:1 and the weight ratio of the agent which facilitates water uptake into the formulation and the pH modulating agent is between 0.5:1 and 1.5:1.

2. A swallow formulation comprising paracetamol particles having a volume median diameter ($D_{50}$) of less than 350 µm and a surface area of greater than 0.07 $m^2 g^{-1}$, a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake into the formulation; wherein at least one pH modulating agent is a carbonate in an amount that will neutralise 0.01 to 9.0 millimoles of hydrochloric acid and is present in an amount from about 1% to 50% by weight of the swallow formulation; wherein at least about 5% of the paracetamol is dissolved from the swallow formulation within 300 seconds at 0 rpm when the dissolution is measured in United States Pharmacopoeia (USP) dissolution apparatus 2 with 900 mL 0.0033 N hydrochloric acid at 37° C., wherein the weight ratio of the paracetamol and the pH modulating agent is between 1.8:1 and 2.5:1 and the weight ratio of the agent which facilitates water uptake into the formulation and the pH modulating agent is between 0.5:1 and 1.5:1.

3. A swallow formulation comprising paracetamol particles having a volume median diameter ($D_{50}$) of less than 350 µm and a surface area of greater than 0.07 $m^2 \cdot g^{-1}$, a pH modulating agent in an amount sufficient to neutralize from about 0.6 mL to about 110 mL 0.1 N hydrochloric acid and/or to neutralize from about 0.06 mmol to about 11 mmol of acid; and an agent which facilitates water uptake into the formulation;
wherein
(a) at least about 5% of the paracetamol is dissolved from the swallow formulation within 300 seconds at 0 rpm, and
(b) at least about 70% of the paracetamol is dissolved from the swallow formulation within 180 seconds at 30 rpm, when the dissolution is measured in United States Pharmacopoeia (USP) dissolution apparatus 2 with 900 mL 0.0033 N hydrochloric acid at 37° C., wherein the weight ratio of the paracetamol and the pH modulating agent is between 1.8:1 and 2.5:1 and the weight ratio of the agent which facilitates water uptake into the formulation and the pH modulating agent is between 0.5:1 and 1.5:1.

4. The swallow formulation of claim 1, wherein at least 80% of the paracetamol is dissolved from the swallow formulation within 180 seconds in USP dissolution apparatus 2 with 900 mL 0.05 N hydrochloric acid at 30 rpm and 37° C.

5. The swallow formulation of claims 2 or 3 wherein the swallow formulation is a tablet and at least 20% of the paracetamol is dissolved from the swallow formulation within 300 seconds in USP dissolution apparatus 2 with 900 mL 0.05 N hydrochloric acid at 0 rpm and 37° C.

6. The swallow formulation of claim 1, wherein at least 80% of the paracetamol is dissolved from the swallow formulation within 120 seconds in USP dissolution apparatus 2 with 900 mL 0.05 N hydrochloric acid at 30 rpm and 37° C.

7. The swallow formulation of claim 1, wherein at least 70% of the paracetamol is dissolved from the swallow formulation within 90 seconds in USP dissolution apparatus 2 with 900 mL 0.05 N hydrochloric acid at 30 rpm and 37° C.

8. The swallow formulation of claim 1, wherein at least 80% of the paracetamol is dissolved from the swallow formulation within 90 seconds in USP dissolution apparatus 2 with 900 mL 0.05 N hydrochloric acid at 30 rpm and 37° C.

9. The swallow formulation of any one of claims 1 to 3 wherein a single dose administration of 1000 mg paracetamol with water in fasted healthy human subjects provides a mean $AUC_{20}$ of more than about 150 min·mg·$L^{-1}$.

10. The swallow formulation of claim 1, wherein a single dose administration of 1000 mg paracetamol with water in fasted healthy human subjects provides a mean $AUC_{20}$ of more than about 170 min·mg·$L^{-1}$.

11. The swallow formulation of claim 1, wherein the paracetamol in the formulation exhibits a dissolution rate in USP dissolution apparatus 2 using 900 mL of 0.05 N hydrochloric acid at 30 rpm and 37° C. of at least 30% in 180 seconds.

12. The swallow formulation of any one of claims 1 to 3 wherein the pH modulating agent is soluble and/or dispersible.

13. The swallow formulation of claim 1, wherein at least one pH modulating agent is a base.

14. The swallow formulation of claim 13, wherein at least one pH modulating agent is a carbonate.

15. The swallow formulation of claim 14, wherein the carbonate is selected from the group consisting of sodium bicarbonate, potassium bicarbonate, calcium carbonate, magnesium carbonate, sodium carbonate, ammonium carbonate, disodium glycine carbonate, sodium glycine carbonate, lysine carbonate and arginine carbonate.

16. The swallow formulation of claim 15, wherein the carbonate is water soluble.

17. The swallow formulation of claim 16, wherein the carbonate is a sodium carbonate.

18. The swallow formulation of any one of claims 1, 2, or 3, wherein the amount of paracetamol dissolved from the swallow formulation is at least about 5 times greater than the amount of rapidly dissolving paracetamol dissolved from a swallow formulation without a carbonate pH modulating agent after 30 seconds in USP dissolution apparatus 2 with 900 mL 0.05 N hydrochloric acid at 30 rpm and 37° C.

19. The swallow formulation of any one of claims 1, 2, or 3, wherein the paracetamol has a volume median diameter ($D_{50}$) less than about 300 μm.

20. The swallow formulation of any one of claims 1, 2, or 3, wherein the paracetamol has a surface area to mass ratio greater than about 0.08 $m^2g^{-1}$.

21. The swallow formulation of any one of claims 1, 2, or 3, wherein the paracetamol is the product of paracetamol crystallized in the presence of one or more crystallization modifiers.

22. The swallow formulation of any one of claims 1, 2, or 3, wherein the paracetamol has been crystallized in the presence of a crystal modifier chosen from the group consisting of polymers, proteins or mixture thereof.

23. The swallow formulation of any one of claims 1, 2, or 3, wherein the paracetamol has been crystallized in the presence of polyvinylpyrrolidone.

24. The swallow formulation of claim 1, wherein the paracetamol is in the form of granules.

25. The swallow formulation of any one of claims 1, 2, or 3, wherein the paracetamol is in the form of granules including an agent chosen from the group consisting of pH modulating agents, water uptake agents and mixtures thereof.

26. The swallow formulation of any one of claims 1, 2, or 3, comprising at least one of extra granular paracetamol, pH modulating agent, or water uptake agent.

27. The swallow formulation of claim 24, wherein the granules further comprise a disintegrant.

28. The swallow formulation of claim 27, wherein the disintegrant is chosen from the group consisting of crospovidone, croscarmellose, sodium starch glycolate, starch, starch derivative and mixtures thereof.

29. The swallow formulation of claims 1, 2, or 3, wherein the agent which facilitates water uptake into the formulation is selected from the group consisting of cross-linked polyvinylpyrrolidone (crospovidone), croscarmellose sodium, sodium starch glycolate, povidone, starch, starch derivatives, low substituted hydroxypropylcellulose, hydroxypropylcellulose, alginic acid, sodium alginate, calcium sulfate, calcium carboxymethylcellulose, microcrystalline cellulose, powdered cellulose, colloidal silicon dioxide, docusate sodium, guar gum, magnesium aluminium silicate, methylcellulose, polacrilin potassium, silicified microcrystalline cellulose, magnesium oxide, tragacanth, mannitol, sorbitol, xylitol, sucrose, lactose, fructose, maltose, polyethylene glycol, aminoacids, cyclodextrin, urea and polyvinylpyrrolidone.

30. The swallow formulation of claims 1, 2, or 3, further comprising one or more other pharmaceutically active agents.

31. The swallow formulation of claim 1, wherein the swallow formulation comprises paracetamol in an amount ranging from 100 mg to 1000 mg, and pH modulating agent in an amount sufficient to neutralize from about 0.3 mL to about 55 mL 0.1N hydrochloric acid and/or to neutralize from about 0.03 mmol to about 5.5 mmol of acid.

32. A dosage form comprising the swallow formulation of claims 1, 2 or 3.

33. A dosage form comprising the swallow formulation of claims 1, 2, or 3, wherein the dosage form is a coated tablet, uncoated tablet, capsule or powder.

34. A dosage form comprising a swallow formulation claims 1, 2, or 3, and selected from the group consisting of coated tablets, uncoated tablets, capsules and powders which further comprises one or more pharmaceutically active agents.

35. A dosage form comprising the swallow formulation of claims 1, 2, or 3, and selected from the group consisting of coated tablets, uncoated tablets, capsules and powders which dosage form comprises a further pharmaceutically active agents comprising paracetamol and wherein the dosage form exhibits dissolution in USP dissolution apparatus 2 using 900 mL of 0.05 N HCl with the paddle spinning at 30 rpm at 37° C. of less than 30% in 180 seconds.

36. A method for the treatment of symptoms chosen from the group consisting of pain, fever, discomfort or combinations thereof in a subject, said method comprising administering to said subject the swallow formulation of any one of claims 1, 2, or 3.

37. A method for the treatment of symptoms chosen from the group consisting of pain, fever, discomfort or combinations thereof and wherein the symptoms are exhibited by a human and the method comprises administering to the human the swallow formulation of any one of claims 1, 2, or 3.

38. The swallow formulation according to claim 30, wherein said one or more other pharmaceutically active agent is an analgesic.

39. The swallow formulation according to claim 38, wherein said analgesic is tramadol.

40. The swallow formulation of claim 15, wherein the carbonate is sodium bicarbonate.

* * * * *